US012667601B2

(12) United States Patent
Ignowski et al.

(10) Patent No.: US 12,667,601 B2
(45) Date of Patent: Jun. 30, 2026

(54) COMPOSITIONS FOR INCREASING RESILIENCE TO TRAUMATIC BRAIN INJURY

(71) Applicant: Immunotec Inc., Vaudreuil-Dorion (CA)

(72) Inventors: Elizabeth E. Ignowski, Vaudreuil-Dorion (CA); Daniel A. Linseman, Littleton, CO (US)

(73) Assignee: IMMUNOTEC INC., Québec (CA)

( * ) Notice: Subject to any disclaimer, the term of this patent is extended or adjusted under 35 U.S.C. 154(b) by 315 days.

(21) Appl. No.: 17/403,025

(22) Filed: Aug. 16, 2021

(65) Prior Publication Data

US 2021/0379145 A1    Dec. 9, 2021

Related U.S. Application Data

(63) Continuation of application No. 16/622,527, filed as application No. PCT/US2018/037535 on Jun. 14, 2018, now abandoned.

(60) Provisional application No. 62/560,424, filed on Sep. 19, 2017.

(30) Foreign Application Priority Data

Jun. 14, 2017    (CA) ................................ CA 2970699

(51) Int. Cl.
    *A61K 38/17*        (2006.01)
    *A61P 25/00*        (2006.01)
(52) U.S. Cl.
    CPC .............. *A61K 38/17* (2013.01); *A61P 25/00* (2018.01)

(58) Field of Classification Search
    None
    See application file for complete search history.

(56) References Cited

U.S. PATENT DOCUMENTS

| | | | |
|---|---|---|---|
| 5,456,924 A | 10/1995 | Bounous | |
| 2013/0330428 A1 | 12/2013 | Geng | |

FOREIGN PATENT DOCUMENTS

EP        2 813 149        12/2014

OTHER PUBLICATIONS

Preclinical Assessment of Immunocal® as a Preventative Treatment for Traumatic Brain Injury (TBI) in a Mouse Model of Closed Head Injury Ignowski, Elizabeth E. University of Denver ProQuest Dissertations Publishing, 2017. 10617715. (Year: 2017).*
Sullivan, Patrick G., et al. "Dietary supplement creatine protects against traumatic brain injury." Annals of neurology 48.5 (2000): 723-729. (Year: 2000).*
International Search Report and Written Opinion of the International Searching Authority, issued Aug. 30, 2018 in corresponding International Patent Application No. PCT/US2018/037535.

(Continued)

*Primary Examiner* — Aurora M Fontainhas
(74) *Attorney, Agent, or Firm* — Wenderoth, Lind & Ponack, L.L.P.

(57)        ABSTRACT

Provided herein are methods, compositions, and uses thereof for preventing traumatic brain injury (TBI) in a subject, wherein a composition comprising whey protein isolate and/or whey protein concentrate may be administered to a subject pre-injury, thereby increasing resilience of the subject to TBI.

16 Claims, 13 Drawing Sheets

(56) References Cited

OTHER PUBLICATIONS

Ignowski et al., "Preclinical Assessment of Immunocal as a Preventative Treatment for Traumatic Brain Injury (TBI) in a Mouse Model of Closed Head Injury", Electronic Theses and Dissertations, XP055500913: (Aug. 15, 2018).

Ross et al., "A Cystine-Rich Whey Supplement (Immunocal) Delays Disease Onset and Prevents Spinal Cord Glutathione Depletion in the hSOD1$^{G93A}$ Mouse Model of Amyotrophic Lateral Sclerosis", Antioxidants, 3(4): 843-865 (2014).

Ross et al., "Immunocal and Preservation of Glutathione as a Novel Neuroprotective Strategy for Degenerative Disorders of the Nervous Systems", Recent Patents on CNS Drug Discovery, 7(3): 230-235 (2012).

Song et al., "Cysteine-rich whey protein isolate (Immunocal) ameliorates deficits in the GFAP.HMOX1 mouse model of schizophrenia", Free Radical Biology and Medicine, 110(8): 162-175 (2017).

Ates, O. et al., Neuroprotection by resveratrol against traumatic brain injury in rat, Mol Cell Biochem 294, 137-144 (2007).

* cited by examiner

C (a)

(b)

A

B

C

D

A

Sham (LT0050)    TBI (LT0038)    TBI+ICAL (LT0153)

B

Luxol fast blue staining
mid-body of corpus callosum

A

B

C

COMPOSITIONS FOR INCREASING RESILIENCE TO TRAUMATIC BRAIN INJURY

FIELD OF INVENTION

The present invention relates generally to methods and compositions for increasing resilience to traumatic brain injury. More specifically, the present invention relates to compositions comprising whey protein isolate and/or concentrate, and their use in protecting against traumatic brain injury.

BACKGROUND

Traumatic brain injury (TBI) is a major public health problem estimated to affect nearly 1.7 million people in the United States annually. Due to the often debilitating effects of TBI, novel preventative agents are highly desirable for at risk populations.

According to the Brain Injury Association of America, nearly 5.3 million Americans are currently living with long term mental or physical disabilities due to TBI. Moreover, the estimated annual cost to society due to TBI in the United States exceeds $76.5 billion. TBI includes injuries to the brain caused by physical trauma resulting from, but not limited to, incidents involving motor vehicles, sporting events, falls, blast injuries, and physical assaults, for example. In addition to short term cognitive, physical or emotional sequelae, TBI may have lasting effects across multiple organs and systems and may cause or accelerate other diseases and disorders that reduce life expectancy.[1]

Based on findings published by the Centers for Disease Control, at least 1.7 million incidences of TBI occur in the United States each year.[2] Of these cases, nearly 75% are categorized as forms of mild TBI including concussions. Repetitive incidences of mild TBI are linked to progressive neurological dysfunction and an increased risk of neurodegeneration. For many decades it has been recognized that repetitive mild TBI experienced by boxers resulted in a syndrome of progressive neurological deterioration originally known as dementia pugilistica. More recently, this term has been replaced with the more descriptive designation, chronic traumatic encephalopathy.[3] This complex neurological disorder is characterized by executive dysfunction, depression, memory impairment, and dementia, amongst other types of cognitive and affective dysfunction.[4] Chronic traumatic encephalopathy and other forms of dementia have been linked to repetitive mild TBI caused by sports related concussive and subconcussive head trauma in football, hockey, soccer, and wrestling.[5-8] In a similar manner, blast-related TBI which is estimated to affect 10-20% of veterans returning from the wars in Iraq and Afghanistan, is also associated with an increased risk of chronic traumatic encephalopathy and other types of dementia, as well as posttraumatic stress disorder.[9,10] Regardless of the cause or severity of TBI, even mild TBI appears to be a significant risk factor for development of dementia including Alzheimer's disease.[11-15] Thus, identification of new strategies to enhance resilience against TBI is of particular importance to people participating in "high risk" occupations, such as athletes or military personnel.

The pathophysiological processes underlying the short and long term injury sequelae associated with TBI are complex. The primary injury is mechanical, resulting from an external force, and leads to tissue deformation, tearing of blood vessels and neuronal axons, necrotic cell death, and initiation of secondary injury processes. Secondary injury mechanisms may include intracranial hemorrhage, excitotoxicity, ionic disturbances, decreased cerebral blood flow, edema, inflammation, mitochondrial dysfunction, oxidative stress, nitrosative stress, and (neuronal and glial) cell death by apoptosis. Although many patients might in theory, be able to significantly recover from the primary mechanical injury of TBI given appropriate acute surgical interventions and supportive care, the detrimental consequences of secondary injury often lead to long term physical, cognitive, and emotional impairments that markedly reduce quality of life. Given the multi-factorial nature of secondary injury, many different therapeutic approaches have been investigated in an attempt to mitigate the post-acute neuronal damage caused by TBI including antioxidants, neurorestorative therapies, neuroprotective pharmacological agents, and drugs that modulate neuroinflammation.[16-22] Yet, despite some compelling results with specific agents in pre-clinical animal models of TBI and Phase I/II trials in patients, there are currently no FDA approved drugs for TBI which have shown significant therapeutic efficacy in large, randomized Phase III clinical trials. Therefore, novel therapeutic approaches for TBI are critically needed.

Oxidative and nitrosative stress are key elements of the secondary injury processes following TBI.[23,24] GSH is an essential antioxidant that detoxifies these free radical species. GSH works in concert with GSH peroxidases, GSH transferases, and peroxiredoxins to detoxify hydroperoxides and other electrophilic species produced during periods of oxidative and nitrosative stress. Several studies suggest that endogenous GSH plays an important protective role against TBI. Brain GSH levels are significantly reduced following TBI induced by controlled cortical impact in rats.[25] Genetic variations in the activity of glutathione-S-transferase-4, a GSH-dependent enzyme that reduces the toxic lipid peroxidation product 4-hydroxynonenal, is a determining factor in the extent of neurodegeneration after TBI in rats.[26] Moreover, mice homozygous for deletion of the GSH-dependent, free radical detoxifying enzyme, glutathione peroxidase-1, display enhanced susceptibility to brain mitochondrial dysfunction induced by TBI.[27]

Several studies have shown that administration of the GSH precursor, N-acetylcysteine, just prior to or immediately after TBI, significantly preserved brain tissue and mitochondrial GSH levels, reduced measures of oxidative damage, and preserved neuronal survival.[28,29] In a similar manner, treatment with another GSH precursor, gamma-glutamylcysteine ethyl ester, reduced indices of oxidative and nitrosative stress and preserved blood-brain-barrier (BBB) function when given immediately post-TBI.[30,31] Finally, the GSH analog and nitric oxide modulator, S-nitrosoglutathione, decreased BBB disruption, minimized neuronal loss, reduced inflammation, protected axonal integrity, and increased the expression of neurotrophic factors when administered post-TBI to rats subjected to controlled cortical impact.[32,33] Enhancing GSH may provide a therapeutic approach for TBI. Unfortunately, few of these previous studies evaluated the effects of GSH precursor supplementation on cognitive or motor deficits induced by TBI and as a result, it has been unclear what therapeutic benefit this strategy might realistically hold for patients suffering from TBI.

The nutritional supplement, IMMUNOCAL®, is a non-denatured whey protein designed to augment the available intracellular GSH pool. Cellular GSH concentrations are highly dependent on the availability of cysteine, which is the limiting precursor in GSH synthesis.[34,35] The cysteine precursor, cystine, occurs at high levels in IMMUNOCAL® because the supplement is rich in serum albumin, alpha-lactalbumin, and lactoferrin. These proteins have a significant number of cystine residues in this non-denatured preparation. In addition, the direct GSH precursor, glutamylcysteine (Baruchel and Viau, 1996; Baruchel et al., 1998), is also found in the serum albumin fraction of this supplement. When cystine is provided in this peptide form, it is resistant to proteolysis by pepsin and trypsin but is readily cleaved and reduced to two cysteine molecules within the target cell. This is significant, as cysteine supplementation alone is cytotoxic.[36] IMMUNOCAL® was initially developed as a nutritional supplement to increase immune system function after dietary amino acids were discovered to increase immune reactivity.[37] It has been investigated in several human diseases and has been shown to significantly increase blood or lymphocyte GSH levels in HIV-seropositive or cystic fibrosis patients, respectively.[38, 39] IMMUNOCAL® is one of only a handful of nutritional supplements that are included in the Physician's Desk Reference and is comprised of natural food protein placing it in the FDA category of generally recognized as safe.[40] IMMUNOCAL® supplementation preserves blood and spinal cord GSH levels and delays disease onset in a transgenic mouse model of amyotrophic lateral sclerosis.[41] In a similar manner, IMMUNOCAL® treatment was recently shown to restore GSH homeostasis in the CNS and ameliorate behavioral deficits in a mouse model of schizophrenia.[42]

Alternative, additional, and/or improved methods and/or compositions for protecting against traumatic brain injury are desirable.

SUMMARY OF INVENTION

In an embodiment, there is provided herein a method for preventing traumatic brain injury (TBI) in a subject, said method comprising:

administering a composition comprising whey protein isolate and/or whey protein concentrate to the subject pre-injury, thereby increasing resilience of the subject to TBI.

In another embodiment, there is provided herein a use of a composition comprising a whey protein isolate and/or a whey protein concentrate for preventing traumatic brain injury (TBI) in a subject, wherein the composition is for increasing resilience of the subject to TBI.

In still another embodiment, there is provided herein a use of a composition comprising a whey protein isolate and/or a whey protein concentrate in the manufacture of a medicament for preventing traumatic brain injury (TBI) in a subject, wherein the medicament is for increasing 5 resilience of the subject to TBI.

In yet another embodiment, there is provided herein a composition comprising a whey protein isolate and/or a whey protein concentrate, for use in preventing traumatic brain injury (TBI) in a subject, wherein the composition is for increasing resilience of the subject to TBI.

In another embodiment of any of the above methods, uses, or compositions for use, the composition may be for administration to the subject at least 2 weeks, at least 3 weeks, or at least 4 weeks prior to injury or prior to performing an activity for which there is a risk of injury. In certain further embodiments, the composition may be for administration to the subject beginning at least about 4 weeks prior to injury or prior to performing an activity for which there is a risk of injury. In still further embodiments, the composition may be for administration to the subject beginning at least about 4 weeks prior to injury or prior to performing an activity for which there is a risk of injury, wherein the composition is for administration at about 20 grams or more per day, for example.

In yet another embodiment of any of the above methods, uses, or compositions for use, the composition may be for administration at about 10 grams to about 20 grams per day for healthy young (<45 years old) individuals; at about 30 grams to about 40 grams per day for older or very athletic individuals; or at about 30 grams to about 40 grams per day or more for individuals with health challenges.

In certain embodiments, the composition may be mixed with water, juice, or milk. In certain embodiments, the composition may be for administration on an empty stomach or with a light meal.

In another embodiment of any of the above methods, uses, or compositions for use, administration of the composition may at least partially prevent reduction in brain GSH/GSSG ratio following injury as compared to an untreated control.

In another embodiment of any of the above methods, uses, or compositions for use, administration of the composition may at least partially prevent motor function and/or cognitive function deficit following injury as compared to an untreated control.

In another embodiment of any of the above methods, uses, or compositions for use, administration of the composition may at least partially preserve corpus callosum width and/or axonal myelination following injury as compared to an untreated control.

In another embodiment of any of the above methods, uses, or compositions for use, administration of the composition may at least partially prevent neuron degeneration following injury as compared to an untreated control.

In another embodiment of any of the above methods, uses, or compositions for use, administration of the composition may at least partially reduce Iba1 microglial marker immunoreactivity in the brain following injury as compared to an untreated control.

In still another embodiment of any of the above methods, uses, or compositions for use, administration of the composition may at least partially reduce demyelination of the corpus callosum following injury as compared to an untreated control.

In another embodiment of any of the above methods, uses, or compositions for use, administration of the composition may at least partially reduce number of foci of degenerating neurons following injury as compared to an untreated control.

In another embodiment of any of the above methods, uses, or compositions for use, the composition may comprise IMMUNOCAL®.

In still another embodiment, there is provided herein a method for preventing or reducing traumatic brain injury (TBI) in a subject, said method comprising:

identifying the subject as being at risk for receiving a TBI based on one or more risk factors;

administering a composition comprising whey protein isolate and/or whey protein concentrate to the subject identified as being at risk for TBI pre-injury, thereby increasing resilience of the subject to TBI.

In another embodiment of the above method, the one or more risk factors may comprise occupational risk, risk associated with planned activities, risk associated with situations or environments to which the subject will be exposed, or a predisposition or susceptibility of the subject to head injury or brain damage.

In another embodiment of any of the above methods, the method may further comprise a step of:

identifying a known risk date on which the subject has elevated risk for TBI based on the one or more risk factors, and identifying a preventative treatment start date which is prior to the known risk date;

wherein administration of the composition to the subject in the step of administering begins on or before the preventative treatment start date. In further embodiments, the preventative treatment start date may be at least 2 weeks, at least 3 weeks, or at least 4 weeks prior to the known risk date.

In certain embodiments, it may be desirable that the preventative treatment start date be at least about 4 weeks prior to the known risk date. In still further embodiments, the preventative treatment start date may be at least about 4 weeks prior to the known risk date, and the composition may be administered at about 20 grams or more per day beginning on the preventative treatment start date, for example. The person of skill in the art having regard to the teachings herein will be aware of suitable dosages and dosage frequencies suitable for a particular individual and/or application. As will be understood, in some cases, the occurrence of a TBI may be difficult to predict and/or to prepare for several weeks in advance; in such circumstances, any increase in resilience to TBI may be preferable to no increase.

In yet another embodiment of any of the above methods the composition may be for administration at about 10 grams to about 20 grams per day for healthy young (<45 years old) individuals; at about 30 grams to about 40 grams per day for older or very athletic individuals; or at about 30 grams to about 40 grams per day or more for individuals with health challenges.

In certain embodiments, the composition may be mixed with water, juice, or milk. In certain embodiments, the composition may be for administration on an empty stomach or with a light meal.

DETAILED DESCRIPTION

Figure 1:
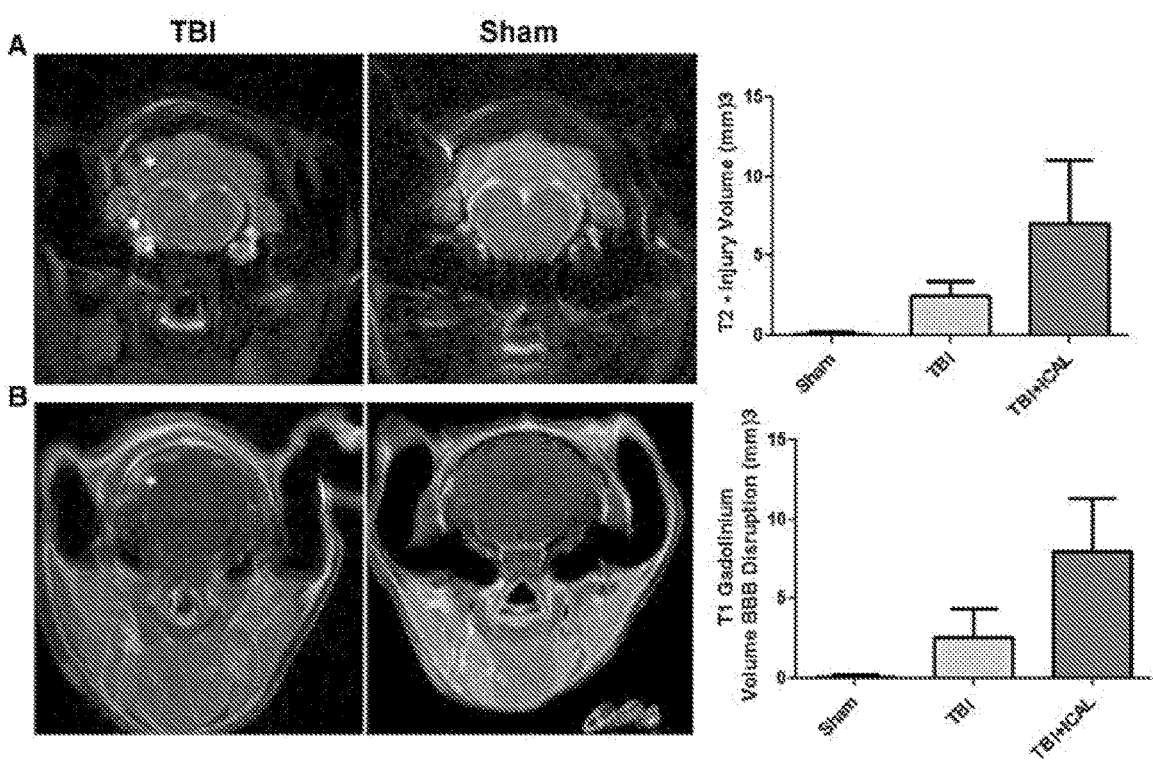
FIG. 1 provides MRI analysis revealing that IMMUNO-CAL® did not protect mouse brain from the primary mechanical injury induced by TBI. A) Representative RARE T2-weighted images of gross brain injury at 72 h post-TBI. The white asterisk indicates an area of injury in a mouse that received a moderate TBI (left) compared to a Sham mouse (right). Corresponding graph shows quantification of the volume of injury in $mm^3$. Results are shown as mean±SEM, n=5-6 mice per group. B) Representative gadolinium-enhanced MSME T1-weighted MR images of BBB disruption at 72 h post-TBI. The white asterisk indicates a hyperintense area of BBB disruption in the same mouse shown in (A) that received a moderate TBI (left) compared to a Sham mouse (right). Corresponding graph shows quantification of the volume of BBB disruption in $mm^3$. Results are shown as mean±SEM, n=5-6 mice per group. C) The graph shows a scatter plot of the data shown in (C). Abbreviations used: BBB, blood-brain-barrier. Abbreviations used: BBB, blood-brain-barrier; ICAL, IMMUNOCAL®.
Figure 1:
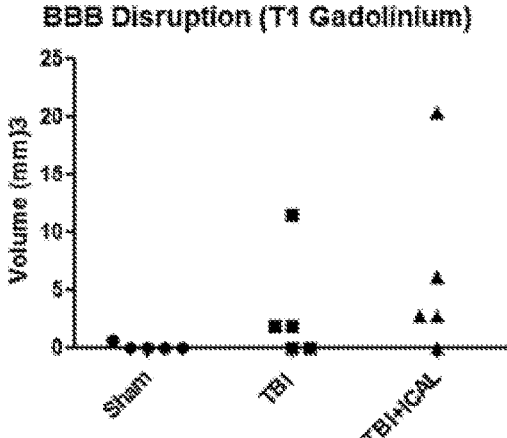

Described herein are methods, compositions, and uses thereof for preventing traumatic brain injury (TBI) in a subject. It will be appreciated that embodiments and examples are provided for illustrative purposes intended for those skilled in the art, and are not meant to be limiting in any way.

In an embodiment, there is provided herein a method for preventing traumatic brain injury (TBI) in a subject, said method comprising:
    administering a composition comprising whey protein isolate and/or whey protein concentrate to the subject pre-injury,
    thereby increasing resilience of the subject to TBI.

In another embodiment, there is provided herein a use of a composition comprising a whey protein isolate and/or a whey protein concentrate for preventing traumatic brain injury (TBI) in a subject, wherein the composition is for increasing resilience of the subject to TBI.

In still another embodiment, there is provided herein a use of a composition comprising a whey protein isolate and/or a whey protein concentrate in the manufacture of a medicament for preventing traumatic brain injury (TBI) in a subject, wherein the medicament is for increasing resilience of the subject to TBI.

In yet another embodiment, there is provided herein a composition comprising a whey protein isolate and/or a whey protein concentrate, for use in preventing traumatic brain injury (TBI) in a subject, wherein the composition is for increasing resilience of the subject to TBI.

As will be understood, preventing TBI and/or increasing resilience of a subject to TBI may be understood as providing an improved resistance to at least one symptom or post-injury effect of TBI, and/or providing an improved recovery from at least one symptom or post-injury effect of TBI. In certain embodiments, compositions as described herein may be considered as preventative or prophylactic treatments to protect a subject at risk of receiving a traumatic brain injury.

In certain embodiments, compositions described herein may be for administration to the subject at least 2 weeks, at least 3 weeks, or at least 4 weeks prior to injury or prior to performing an activity for which there is a risk of injury.

Generally, treatment with IMMUNOCAL® for about 2 weeks at about 20 grams per day optimizes whole blood GSH in man. Since GSH whole blood levels do not always correlate with cerebral GSH levels, it may be desirable in certain embodiments that the composition be for administration to the subject beginning at least about 4 weeks prior to injury or prior to performing an activity for which there is a risk of injury. In still further embodiments, the composition may be for administration to the subject beginning at least about 4 weeks prior to injury or prior to performing an activity for which there is a risk of injury, wherein the composition is for administration at about 20 grams or more per day, for example. The person of skill in the art having regard to the teachings herein will be aware of suitable dosages and dosage frequencies suitable for a particular individual and/or application. As will be understood, in some cases, the occurrence of a TBI may be difficult to predict and/or to prepare for several weeks in advance; in such circumstances, any increase in resilience to TBI may be preferable to no increase.

In certain embodiments, the composition may be for administration at about 10 grams to about 20 grams per day for healthy young (<45 years old) individuals; at about 30 grams to about 40 grams per day for older or very athletic individuals; or at about 30 grams to about 40 grams per day or more for individuals with health challenges.

In still further embodiments, the composition may be mixed with water, juice, or milk. In certain embodiments, mixing with hot beverages may be avoided. In certain embodiments, the composition may be for administration on an empty stomach or with a light meal.

In certain embodiments, methods and uses described herein may include a step of identifying a subject at risk of receiving a traumatic brain injury prior to administration of the composition. This skilled person having regard to the teachings herein will be able to identify suitable criteria for identifying a subject as being at risk based on any of a variety of factors which may be associated with an increased risk or susceptibility to TBI. Factors may include, for example but not limited to, the subject's occupation, planned activities (such as sports or hobby activities), physical condition, and/or a predisposition or susceptibility of the subject to head injury or brain damage (for example, due to physical condition, falls, surgery, stroke, etc. . . . ), or any other suitable factor or combination thereof. By way of example, individuals with previous concussion or traumatic brain injury history may be more prone to future injury, and may therefore be identified as being at risk and may be counselled on the benefit of prophylaxis.

Accordingly, in certain embodiments, there is provided herein a method for preventing traumatic brain injury (TBI) in a subject, said method comprising:

identifying the subject as being at risk for receiving a TBI based on one or more risk factors;

administering a composition comprising whey protein isolate and/or whey protein concentrate to the subject identified as being at risk for TBI pre-injury, thereby increasing resilience of the subject to TBI.

In certain embodiments, the one or more risk factors may comprise occupational risk, risk associated with planned activities, or a predisposition or susceptibility of the subject to head injury or brain damage.

In certain embodiments, where the subject is identified as being at risk for receiving a TBI due to a risk factor having a known date (such as participation in a planned high risk sport, for example), a preventative treatment start date may be determined which is prior to the known date, thereby increasing resilient of the subject to TBI by the known date as compared to no treatment.

In certain embodiments, the preventative treatment start date may be at least 2 weeks, at least 3 weeks, or at least 4 weeks prior to the known date. It may be desirable in certain embodiments that the preventative treatment start date be at least about 4 weeks prior to the known date. In still further embodiments, the preventative treatment start date may be at least about 4 weeks prior to the known date, and the composition may be administered at about 20 grams or more per day beginning on the preventative treatment start date, for example. The person of skill in the art having regard to the teachings herein will be aware of suitable dosages and dosage frequencies suitable for a particular individual and/or application. As will be understood, in some cases, the occurrence of a TBI may be difficult to predict and/or to prepare for several weeks in advance; in such circumstances, any increase in resilience to TBI may be preferable to no increase.

In certain embodiments, the composition may be for administration at about 10 grams to about 20 grams per day for healthy young (<45 years old) individuals; at about 30 grams to about 40 grams per day for older or very athletic individuals; or at about 30 grams to about 40 grams per day or more for individuals with health challenges.

In still further embodiments, the composition may be mixed with water, juice, or milk. In certain embodiments, mixing with hot beverages may be avoided. In certain embodiments, the composition may be for administration on an empty stomach or with a light meal.

In another embodiment of any of the above methods, uses, or compositions for use, administration of the composition may at least partially prevent reduction in brain GSH/GSSG ratio following injury as compared to an untreated control.

In another embodiment of any of the above methods, uses, or compositions for use, administration of the composition may at least partially prevent motor function and/or cognitive function deficit following injury as compared to an untreated control.

In another embodiment of any of the above methods, uses, or compositions for use, administration of the composition may at least partially preserve corpus callosum width and/or axonal myelination following injury as compared to an untreated control.

In another embodiment of any of the above methods, uses, or compositions for use, administration of the composition may at least partially prevent neuron degeneration following injury as compared to an untreated control.

In another embodiment of any of the above methods, uses, or compositions for use, administration of the composition may at least partially reduce Iba1 microglial marker immunoreactivity in the brain following injury as compared to an untreated control.

In still another embodiment of any of the above methods, uses, or compositions for use, administration of the composition may at least partially reduce demyelination of the corpus callosum following injury as compared to an untreated control.

In another embodiment of any of the above methods, uses, or compositions for use, administration of the composition may at least partially reduce number of foci of degenerating neurons following injury as compared to an untreated control.

In yet another embodiment, the whey protein isolate and/or whey protein concentrate may be or comprise IMMUNOCAL®, or a functional equivalent thereof. In still another embodiment, the composition may further comprise a pharmaceutically acceptable excipient, carrier, or diluent.

In yet another embodiment, the whey protein isolate and/or whey protein concentrate may be substantially undenatured.

Compositions described herein may comprise whey protein isolate and/or whey protein concentrate, which is a source of the glutathione precursor cysteine.

Compositions comprising whey protein isolate and/or whey protein concentrate may comprise any suitable composition comprising whey protein isolate and/or whey protein concentrate which may serve as a glutathione precursor by providing an enriched source of bioavailable cysteine after administration. As will be understood, whey proteins may generally be considered as a group a milk proteins which remain soluble in "milk serum" or whey after precipitation of caseins at pH 4.6 and 20° C. Major whey proteins in cow's milk, for example, may include beta-lactoglobulin (βL), alpha-lactalbumin (αL), immunoglobulin, and serum albumin (SA). The product of industrial separation of this protein mixture from whey is typically referred to as whey protein isolate (WPI; also known as whey protein concentrate, WPC).

Compositions may, optionally, additionally comprise one or more pharmaceutically acceptable excipients, diluents, and/or carriers, one or more vitamins, essential amino acids, or minerals, one or more antioxidants, one or more additional glutathione precursors, and/or one or more nutritional diet supplement components, for example.

In certain embodiments, compositions comprising whey protein isolate and/or whey protein concentrate may additionally comprise one or more pharmaceutically acceptable carriers, diluents, or excipients which may include any suitable carrier, diluent, or excipient known to the person of skill in the art. Examples of pharmaceutically acceptable excipients may include, but are not limited to, cellulose derivatives, sucrose, and starch. The person of skill in the art will recognize that pharmaceutically acceptable excipients may include suitable fillers, binders, lubricants, buffers, glidants, and disentegrants known in the art (see, for example, Remington: The Science and Practice of Pharmacy (2012); herein incorporated by reference in its entirety). Examples of pharmaceutically acceptable carriers, diluents, and excipients may be found in, for example, Remington's Pharmaceutical Sciences (2000—20th edition) and in the United States Pharmacopeia: The National Formulary (USP 40 NF35) published in 2017.

In certain embodiments, a whey protein isolate or a whey protein concentrate as described herein may include any suitable extract, isolate, concentrate, or other product which is obtainable from whey protein. As will be understood, whey protein comprises a mixture of milk proteins that remain soluble in milk serum or whey after precipitation of caseins, for example. Whey is often encountered as a by-product of cheese or casein manufacture. Major whey protein components may include, for example but without wishing to be limiting, beta-lactoglobulin, alpha-lactalbumin, immunoglobulin, and/or serum albumin. Although bovine milk is commonly used for obtaining whey protein, it will be understood that other sources of milk are also contemplated. Whey protein isolate (WPI) is generally considered in the field as having ≥90% protein, while whey protein concentrate (WPC) may have protein concentrations below 90%; however, for the present purposes, WPI and WPC may be considered as generally interchangeable unless otherwise explicitly specified.

In particular embodiments, a whey protein isolate or whey protein concentrate as described herein is preferably a substantially undenatured whey protein isolate or whey protein concentrate. Undenatured isolates and concentrates are those in which one or more of the protein component(s) obtainable from whey protein remain substantially undenatured (i.e. tertiary protein structure is substantially maintained and/or disulfide bonds between cysteine residues remain substantially intact) in the whey protein isolate or whey protein concentrate.

Whey proteins contain sulfur-containing amino acids such as cysteine (Cys). These Cys amino acid residues may occur as free residues (i.e. —SH; reduced), or two Cys residues may form intramolecular disulfide bonds (S—S; oxidized) so as to produce cystine dimers. Such disulfide bonds play a role in protein folding. In certain embodiments, undenatured whey protein isolates or whey protein concentrates as described herein may include those having at least about 2 wt % cystine dimer. Examples of undenatured whey protein isolates and whey protein concentrates may include those having about 2 wt % cystine dimer, or more than about 2 wt % cystine dimer. For example, the wt % of cystine dimer may be about 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, or 4.0 wt %, or the wt % cystine dimer may fall within a range spanning between any two such values, or a range bounded at the lower end by any such value.

Whey protein isolates and whey protein concentrates may be obtained using any suitable technique(s) as will be known to the person of skill in the art having regard to the teachings herein. Such techniques may include ultrafiltration using membranes, ion exchange methods, and membrane methods, for example. Discussions of suitable techniques may be found in, for example, Advanced Dairy Chemistry, McSweeney and Mahony (Ed.), Volume 1B: Proteins: Applied Aspects, 4th Edition, Springer, ISBN: 978-1-4939-2799-9 (herein incorporated by reference in its entirety).

Examples of suitable compositions comprising whey protein isolate and/or whey protein concentrate are described in Canadian patent nos. 1,333,471, 1,338,682, 2,142,277, and 2,090,186, each of which is herein incorporated by reference in its entirety. CA 2,142,277, for example, provides detailed preparation processes and analytical characterization of particularly preferred compositions comprising whey protein isolate, including the composition known as IMMUNO-CAL®. This exemplary whey protein isolate composition as described in CA 2,142,277 may be characterized by having a solubility index of about 99.5% at pH 4.6; about 58% βL (beta-lactoglobulin) protein composition, about 11% αL (alpha-lactalbumin) protein composition, about 10% serum albumin (i.e. BSA) protein composition, and about 22% immunoglobulin (i.e. Ig) protein composition. A process for preparing such a composition is also described in detail in CA 2,142,277. IMMUNOCAL® (Natural Product Number (NPN) 80004370 issued with Health Canada) is now a commercially available whey protein isolate composition available from Immunotec®.

Further description of whey protein isolates and concentrates may be found in Example 2 below.

In an embodiment, compositions as described herein may be administered orally. For example, compositions as described herein may be reconstituted in, or may comprise, a liquid carrier (for example, water or juice), or a semi-liquid carrier (for example, yoghurt or apple sauce), allowing for straightforward oral administration. The person of skill in the art having regard to the teachings herein will be able to select a suitable administration to suit a particular subject and/or particular therapeutic application.

In certain non-limiting embodiments, it is contemplated that compositions as described herein may be administered orally in an amount suitable for achieving a desired effect. In certain non-limiting embodiments, compositions as described herein may be administered orally in a dosage of about 20-40 grams per day, for example, and may be administered once or more than once daily, for example.

It will be understood that compositions as described herein may be administered as part of a treatment regimen including other drugs, pharmaceutical compositions, or therapies used in the treatment of TBI. Compositions as described herein may be for administration simultaneously, sequentially, in combination with, or separately from such other drugs, pharmaceutical compositions, or therapies. In certain embodiments, whey protein isolate/concentrate such as IMMUNOCAL® may be administered through a nasogastric feeding tube.

As will be understood, compositions comprising whey protein isolate and/or whey protein concentrate as described herein may serve as a glutathione precursor by providing an enriched source of bioavailable cysteine following administration.

Example 1—Traumatic Brain Injury (TBI) Prevention Studies Using IMMUNOCAL®

It was hypothesized that a strategy aimed at sustaining or enhancing brain GSH levels may be a viable approach to mitigate secondary injury and the subsequent long term cognitive, physical, and emotional deficiencies induced by TBI. It was further hypothesized that supplementation with whey protein isolate/concentrate such as IMMUNOCAL® prior to TBI in mice may provide enhanced resilience against oxidative damage, neuronal cell death, and/or cognitive and/or motor impairments induced by a closed head impact injury.

Accordingly, here, a whey protein supplement, IMMU-NOCAL®, was tested for its potential to enhance resilience to TBI. IMMUNOCAL® is a non-denatured whey protein preparation which has been shown to act as a cysteine delivery system to increase levels of the essential antioxidant glutathione (GSH). Twice daily oral supplementation of CD1 mice with IMMUNOCAL® for 28 days prior to receiving a moderate TBI prevented an ~25% reduction in brain GSH/GSSG observed in untreated TBI mice. IMMU-NOCAL® had no significant effect on the primary mechanical injury induced by TBI, as assessed by MRI, changes in Tau phosphorylation, and righting reflex time or apnea. However, pre-injury supplementation with IMMUNO-CAL® resulted in statistically significant improvements in motor function (beam walk and rotarod) and cognitive function (Barnes maze). A significant preservation of corpus callosum width (axonal myelination), a significant decrease in degenerating neurons, a reduction in Iba1 (microglial marker) immunoreactivity, decreased lipid peroxidation, and preservation of brain-derived neurotrophic factor (BDNF) in the brains of IMMUNOCAL®-pretreated mice compared to untreated TBI mice was also observed. Taken together, these data indicate that pre-injury supplementation with IMMU-NOCAL® may significantly enhance the resilience to TBI induced by a moderate closed head injury in mice. Based on these results, IMMUNOCAL® may be used a preventative agent for TBI, particularly in certain high risk populations such as athletes and military personnel.

Materials and Methods

Animal Care and Treatment

All animal work was conducted under a protocol approved by the University of Denver Institutional Animal Care and Use Committee. Male CD1 Elite mice (35 days-old) were purchased from Charles River Laboratories (Hollister, CA). Mice received a numbered ear tag upon arrival for identification purposes, and then were allowed one week to acclimate to the animal facility at the University of Denver before beginning the study. Mice were then randomly assigned and evenly distributed among one of three treatment groups: Sham, TBI, or TBI+IMMUNOCAL®. Mice in the TBI+IMMUNOCAL® group were dosed twice daily by oral gavage with 0.25 mL of a 3.3% solution of IMMUNOCAL® in sterile drinking water. Dosing was performed 5 days a week over a period of 28 days prior to TBI. This dosing regimen has previously been shown to yield positive therapeutic effects in a mouse model of amyotrophic lateral sclerosis.[40] The day on which TBI was induced was considered "day 0". Following TBI, mice were monitored closely each day for signs of infection, bleeding, and general distress until the main study concluded on day 18. The magnetic resonance imaging session (described below) concluded on day 3.

Traumatic Brain Injury

Following the 28-day IMMUNOCAL® dosing regimen, TBI was induced by controlled cortical impact using the Leica Impact One system (Leica Biosystems, Buffalo Grove, IL). Briefly, mice were anesthetized using an isoflurane vaporizer (VetEquip, Inc., Livermore, CA) and monitored throughout the procedure for the depth of anesthesia by toe pinch reflex. While anesthetized, temperature was maintained at approximately 37±1° C. by placement on a thermal pad. A midline incision approximately 1 cm in length was made along the head and the skin was pulled aside using small bulldog clamps. Bupivacaine (0.25% solution in sterile water) was applied generously to the open incision. With the skull exposed, a dental scraper was used to partially remove the fascia in order to better visualize anatomical markers. Bregma was located, and a concave 22-gauge stainless steel disk, 5 mm in diameter, was affixed to the skull using tissue adhesive just caudal to this point. Animals were then placed into a stereotaxic frame (Braintree Scientific Inc., Braintree, MA) and the head was secured to prevent movement during impact. The arm of the impactor was then positioned such that the impactor probe (5 mm diameter) was directly centered over the metal disk. The probe was then set to the desired impact depth of 2.75 mm and a velocity of 5.875 (±0.125) m/s (dwell time 100 msec) to induce a moderate injury as described by Lloyd et al. (2008).[43] Mice in the TBI and TBI+IMMUNOCAL® groups were subjected to injury at this time, after which animals were monitored for signs of TBI-induced apnea. Once apnea was overcome, animals were removed from the stereotaxic frame. Sham animals were not subjected to impact and were simply removed from the stereotaxic frame following identification. Mice were returned to the thermal pad, the metal disk was removed from the skull, and the incision was then closed using tissue adhesive. The mice were allowed to recover on the thermal pad during which time their righting reflex times were measured. Righting reflex was defined as the point at which the animal was able to return to and maintain a sternal position after being placed on its side during recovery from anesthesia. Mice were returned to their home cage once they became fully ambulatory.

Behavioral Assays of Cognitive and Motor Function

Challenging Beam Walk Task

The challenging beam walk task for motor function and coordination was performed as previously described by Fleming et al. (2013).[44] The apparatus for the challenging beam walk was composed of four segments supplied by Starks Plastics (Forest Park, OH), each of which was 25 cm in length. The first segment had a width of 3.5 cm, with each subsequent section decreasing by one centimeter in width to a final measurement of 0.5 cm. These segments were secured together and suspended at a height of approximately 14.5 cm above a level surface. Mice were allowed a two-day training period prior to TBI on days −2 and −1. On the first training day, mice were placed at the wide end of the beam. The investigator then held an empty cage containing clean bedding on its side a few centimeters in front of the mouse as incentive for the animal to navigate the beam. As the mouse moved toward the cage, the investigator pulled the cage away from the mouse such that the animal was forced to traverse the beam and the mouse was only allowed to enter the cage once it had successfully reached the end of the beam. This procedure was repeated until the mouse could traverse the beam without the need for prompting or correction from the investigator. On the following day, a cage with clean bedding was placed on its side at the narrow end of the beam in a fixed position. Mice were then placed on the wide end of the beam and allowed to traverse the full length of the beam to reach the empty cage. This phase of training was repeated until the mouse could consistently traverse the entire beam without prompting or correction from the investigator.

Following TBI induction (or Sham surgery) on day 0, mice entered the testing phase of the challenging beam walk task on day 1. For this phase, wire grids with openings measuring 1 cm$^2$ were placed securely over each beam segment creating a space between the top of the grid and the surface of the beam. This was done to increase the difficulty of the task and to enhance visual scoring of foot faults. As before, an empty cage was placed at the narrow end of the beam and served as the goal for successful completion of the beam walk. Mice were placed at the wide end of the beam on top of the grid and allowed to traverse the entire length of the beam a total of three times, with each traversal of the beam recorded using a video camera. The number of foot faults for the right hind foot was quantified for each animal on each segment of the beam and averaged across the three attempts. Foot faults were defined as any point at which the mouse stepped through the metal grid or gripped the plastic beam instead of the wire grid. The time it took the mouse to traverse the full length of the beam was also recorded for each of the three attempts on the beam, and the percentage change in time taken to traverse the beam between trial 1 and trial 3 for each mouse was calculated.

Modified Y Maze

Following the challenging beam walk, mice were tested on Day 1 in a modified version of the Y-maze (Stoelting, Wood Dale, IL) designed to test spatial recognition and working memory as described by Adamczyk et al. (2014). In the first phase of testing, one arm of the maze was blocked. The mouse was placed into the entry arm, and allowed to explore the open areas of the maze for a period of 5 minutes without interference. After this period, the mouse was removed from the maze and returned to its home cage for a period of 10-15 minutes. The blocked arm of the maze was then opened. The mouse was again placed into the entry arm and allowed an additional 5 minutes to explore the entirety of the maze. The time it took the animal to enter the newly opened arm was recorded as lag time, and the time spent in the unblocked arm versus the two previously opened arms was determined. Additionally, the number of entries into each arm were quantified to ensure that all mice were equally active throughout the testing period.

Accelerating Rotarod

Rotarod testing for motor coordination and function was performed on days 9 and 16 following TBI (or Sham surgery). Mice were placed on a rod, 30 mm in diameter, rotating at 4 rpm. Animals were placed in individual lanes to prevent interference between mice while the test was being conducted. When the mice had acclimated to the slow speed, the rod was accelerated from 4 rpm to 40 rpm over the course of 5 minutes. Mice were given three attempts on the apparatus before testing ended. The duration of time that the mouse spent on the rod was recorded by depression of a lever triggered upon the mouse falling and the recorded values were averaged across the three attempts.

Barnes Maze

Barnes maze (ANY-maze, Wood Dale, IL) testing was performed on days 10-16 post-TBI, as described by Mouzon et al. (2012).[45] The first 6 days of testing comprised the acquisition phase, followed by a single probe/test day. The circular maze was divided into quadrants with an arrow on the wall used as a visual cue to identify the location of the escape pod. During the acquisition phase, mice were placed in each quadrant and allowed 90 sec to find the escape pod. If the mice were unable to find the pod after the allotted time, they were directed to it and remained in the pod for 30 sec. If they found the pod and entered on their own, the pod was then covered and they remained there for 30 sec. Videos were reviewed and latency times to find the escape pod were recorded. On the probe day, the pod was blocked so that mice could not enter. Mice were placed in the middle of the maze and allowed to search the maze for 60 sec. Videos were reviewed and latency times to the escape pod zone (encompassing the escape pod and either pod directly adjacent to it) were recorded.

Reagents

Primary antibodies to beta actin, S100beta and Iba-1 were purchased from Abcam (Cambridge, MA). The primary antibodies to Tau phosphorylated on Ser396, Thr231, and Ser404, as well as total Tau, were purchased from Invitrogen (Carlsbad, CA). Primary antibody to BDNF was from Alomone Labs (Jerusalem, Israel). Primary antibody to PHF-Tau was from Thermo Scientific (Waltham, MA). Primary antibody to GFAP was purchased from Abcam (Cambridge, MA). Purified oxidized (GSSG) and reduced (GSH) glutathione was purchased from Sigma Aldrich Co. LLC (St. Louis, MO). Cy3-conjugated secondary antibody was purchased from Jackson Immunoresearch (Westgrove, PA). Fluoro-Jade C staining kit was purchased from Biosensis (Temecula, CA). Luxol fast blue staining kit was purchased from American Mastertech (Lodi, CA). Malondialdehyde (MDA) lipid peroxidation assay kit was obtained from Abcam (Cambridge, MA) and the assay was conducted essentially as described by the manufacturer.

Fluoro-Jade C Staining for Degenerating Neurons

Tissue Processing

Frozen whole brains, excluding cerebellum, were cryosectioned either by the Histology Core at the University of Colorado Anschutz medical campus or AML Laboratories Inc. (St. Augustine, FL). Briefly, 12 μm coronal sections were created starting at bregma and proceeding towards the posterior of the brain. Tissue sections were mounted on adhesive microscope slides discarding three to four tissue sections between each mounting. Following mounting, tissue was fixed in 4% paraformaldehyde for one hour.

Slide Staining

Fluoro-Jade C staining was performed as specified by the manufacturer. Briefly, coronal brain sections were immersed in a 1:9 (v/v) solution of 1% sodium hydroxide and 70% ethanol for five minutes, followed by a two-minute wash in 70% ethanol. Next, tissue sections were immersed in a 1:9 (v/v) solution of 0.06% potassium permanganate and distilled water for ten minutes and then washed with distilled water for two minutes. Tissue was then incubated in a 1:2:8 (v/v/v) solution of DAPI, 0.0004% Fluoro-Jade C and distilled water for ten minutes, taking precaution to protect the solution from light. Sections were then washed three times in distilled water and dried at 50-60° C. for ten minutes. Sections were imaged under 40× magnification on a Zeiss Axiovert-200M fluorescence microscope using a FITC filter and in a blinded fashion, to identify fluorescent foci of degenerating neurons. The total number of Fluoro-Jade C-positive foci were then quantified for at least two tissue sections per mouse.

Luxol Fast Blue Staining

Tissue processing was done as described above for Fluoro-Jade C staining. Brain sections were incubated in Luxol fast blue stain solution at 60° C. overnight, followed by washing with distilled water. Sections of gray and white matter were differentiated by dipping brain tissue into 0.05% lithium carbonate and 70% ethanol. Slides were then immersed in cresyl violet stain for ten minutes followed by further differentiation in 70% ethanol. Following the staining process, tissue sections were imaged at 20× magnification to visualize the corpus callosum. Images of the mid-body of the corpus callosum were captured for at least two tissue sections per animal. The health of the corpus callosum was assessed by measuring the maximum width of the mid-body.

Magnetic Resonance Imaging (MRI)

All MRI studies were performed in the Colorado Animal Imaging Shared Resources (University of Colorado Anschutz Medical Campus, Aurora, CO). All animals underwent an MRI session 72 hours after TBI (or Sham surgery), using pre- and post-gadolinium-enhanced (0.2 mmol/kg Omniscan® IV) T1-weighted and T2-weighted sequences.[46] The mice were anesthetized with 2.5% isoflurane, placed into an animal holder and inserted into a 4.7 Tesla Bruker PharmaScan. A quadrature birdcage coil (inner diameter 38 mm) tuned to the 1H frequency of 200.27 MHz, was used for RF transmission and reception. T2-weighted MRI (to confirm and quantify injury) was acquired using a rapid acquisition with relaxation enhancement (RARE, Bruker manufacturer label for a fast spin echo sequence) protocol with the following parameters: Field of view (FOV)=36 mm; repetition time/echo time (TR/TE)=4,000/100 msec; slice thickness=1 mm; no interslice gaps; number of slices=16; number of averages=8; matrix size=128×256; total acquisition time=8 min 31 sec. T1-weighted MR images (for BBBD assessment) were acquired using a multi-slice multi-echo (MSME, Bruker manufacturer label for a spin echo sequence, in this case with one echo) sequence, before and 5 minutes after administration of 0.2 mmol/kg Omniscan® via tail vein. The following acquisition parameters were used: FOV=36 mm; TR/TE=900/11 msec; slice thickness=1 mm with no gaps applied; number of slices=16; number of averages=2; matrix size=128×256; total acquisition time=3 min 50 sec. All images were acquired in the axial plane. All images analysis was performed using Bruker Para Vision v4.1 software.

Western Blotting

Whole half brains, excluding cerebellum, were thawed from liquid nitrogen. A 1 mL aliquot of lysis buffer was added, with 1 μL of leupeptin (5 mg/mL) and 1 μL of aprotinin (5 mg/mL), per half brain. The brains were then homogenized using a Dounce glass/glass homogenizer by 20 strokes with the loose pestle followed by 20 strokes with the tight pestle. Samples were centrifuged for 5 min at 10,000 rpm, and the supernatant was isolated. The samples were diluted 1:100 for a BCA protein assay. Western immunoblotting was done to immunochemically detect proteins immobilized on polyvinylidene difluoride (PVDF) membranes. Protein samples (80 μg/lane) were resolved by SDS-PAGE and proteins were then transferred to PVDF membranes. Non-specific binding sites were blocked using 1% BSA in phosphate-buffered saline (pH 7.4) containing 0.1% Tween-20 (PBS-T) for 1 h at 25° C. The blocking buffer was drained and the membrane was allowed to incubate in primary antibody diluted in blocking buffer overnight at 4° C. The membrane was washed 3× for 15 min in PBS-T and was then incubated with the secondary antibody for 1.5 h at 25° C. The secondary was then removed and the membrane was washed again in PBS-T, 3× for 15 min. Immunoreactive proteins were detected using enhanced chemiluminescence (GE Healthcare; Pittsburgh, PA) and films were developed using a CP 1000 developer (AGFA; Mortsel, Belgium).

Immunofluorescence Microscopy

Sections of cortex were stained for the astrocyte marker, glial fibrillary acidic protein (GFAP), and nuclei were stained with DAPI, using a standard immunohistochemistry protocol. GFAP-positive astrocytes were detected using a Cy3-conjugated secondary antibody.

High Performance Liquid Chromatography with Electrochemical Detection (HPLC-ECD)

Tissue Processing

Full half brains, excluding cerebellum, were obtained from mice 72 h post-TBI (or Sham surgery) and were immediately frozen in liquid nitrogen. For HPLC-ECD analysis, a previously published procedure was utilized (Ross et al., 2014). Briefly, 2.5M perchloric acid was added to each half brain and the brains were roughly chopped using pointed surgical scissors. Samples were then sonicated 3 times for 15 s intervals. Samples were then centrifuged for 5 min at 13,000 rpm and the supernatant was removed. A 20 μL aliquot of the supernatant was used for a BCA protein assay. The remainder of each solution was neutralized with 500 μL of 4M KOH and vortexed thoroughly. Samples were then centrifuged for 15 min at 13,000 rpm, and stored at −80° C. until separation and analysis by HPLC-ECD.

HPLC-ECD

GSH and GSSG in samples and known standards were separated by reversed-phase HPLC on a C18 bonded silica column at 35° C. (5 μm, 4.6×250 mm) from Dionex, Inc. (Sunnyvale, CA). Analytes were detected using a CoulArray® detector (model 5600, ESA) on three coulometric array cells in series; electrochemical detectors were set between 0 and 900 mV at increments of 75 mV. Concentrations were determined with a standard curve of each identified analyte. Mobile phase consisted of 50 mM lithium acetate and 1% acetonitrile in water, pH 3.8. The flow rate was set to 0.4 mL/min for all samples. CoulArray® software was used for baseline correction and peak analysis.

Statistical Analysis

Data presented are shown as the mean±SEM for the number (n) of independent experiments performed. An independent set of mice consisted of a single mouse from each group (Sham, TBI, TBI+IMMUNOCAL®). Statistical differences between groups were evaluated using either one-way ANOVA with a post-hoc Tukey's test or paired/unpaired Student's t-tests. Effect sizes and corresponding 95% confidence intervals are also shown within the Figure Legends. Data analysis of behavioral tests was performed by observers blinded to the group assignments of the mice. Similarly, microscopic analysis of Fluorojade-C- and luxol fast blue-stained slides was performed by observers blinded to the group assignments of the mice. Finally, MRI analysis of BBB permeability was also performed and quantified by an observer blinded to the group assignments of the mice.

Results

Pre-Injury Supplementation with IMMUNOCAL® Did not Affect the Primary Mechanical Injury Induced by a Moderate TBI Throughout the study, mice were equally divided into the following three groups: Group 1, Sham surgery controls; Group 2, untreated TBI mice; and Group 3, mice pretreated with IMMUNOCAL® for 28 days prior to TBI. The extent of brain injury was initially assessed at 72 h post-TBI by MRI analysis. T2 weighted imaging demonstrated areas of damaged brain tissue in mice subjected to TBI (FIG. 1A, image panels; see asterisk in the TBI image which marks an area of injury). The same region of brain which demonstrated damage in the T2 weighted image also showed a hyper-intense area which indicates BBB disruption in the corresponding T1 weighted image taken with gadolinium contrast (FIG. 1B, image panels; see asterisk in the TBI image which marks an area of BBB disruption). In general, areas of brain injury and BBB disruption were exclusively observed in mice subjected to TBI but not Sham controls. In addition, areas of injury appeared primarily in the outer layers of the cortex and were most often seen in the region caudal to bregma (i.e., the region of impact). However, brain injury was not confined solely to the midline of the brain, but also extended to either side of the midline. This latter observation is characteristic of this TBI model where the impactor probe hits a metallic disk affixed to the closed skull, causing a diffusion of the injury throughout the cortex. Quantification of the volume of injury observed in the T2 weighted images and the volume of BBB disruption indicated by the T1 weighted, gadolinium-enhanced images revealed no significant differences between the untreated TBI group and the IMMUNOCAL®-pretreated TBI group (FIGS. 1A and 1B, bar graphs). In a scatter plot of these data, it is evident that 3 out of 5 untreated TBI mice and 4 out of 5 IMMUNOCAL®-pretreated TBI mice displayed measurable BBB disruption (FIG. 1C). These data indicate that the overall magnitude of brain injury induced by the TBI procedure was comparable for each group of mice and moreover, pre-injury supplementation with IMMUNO-CAL® had no discernible protective effect against the primary mechanical injury induced by a moderate TBI.

Figure 2:
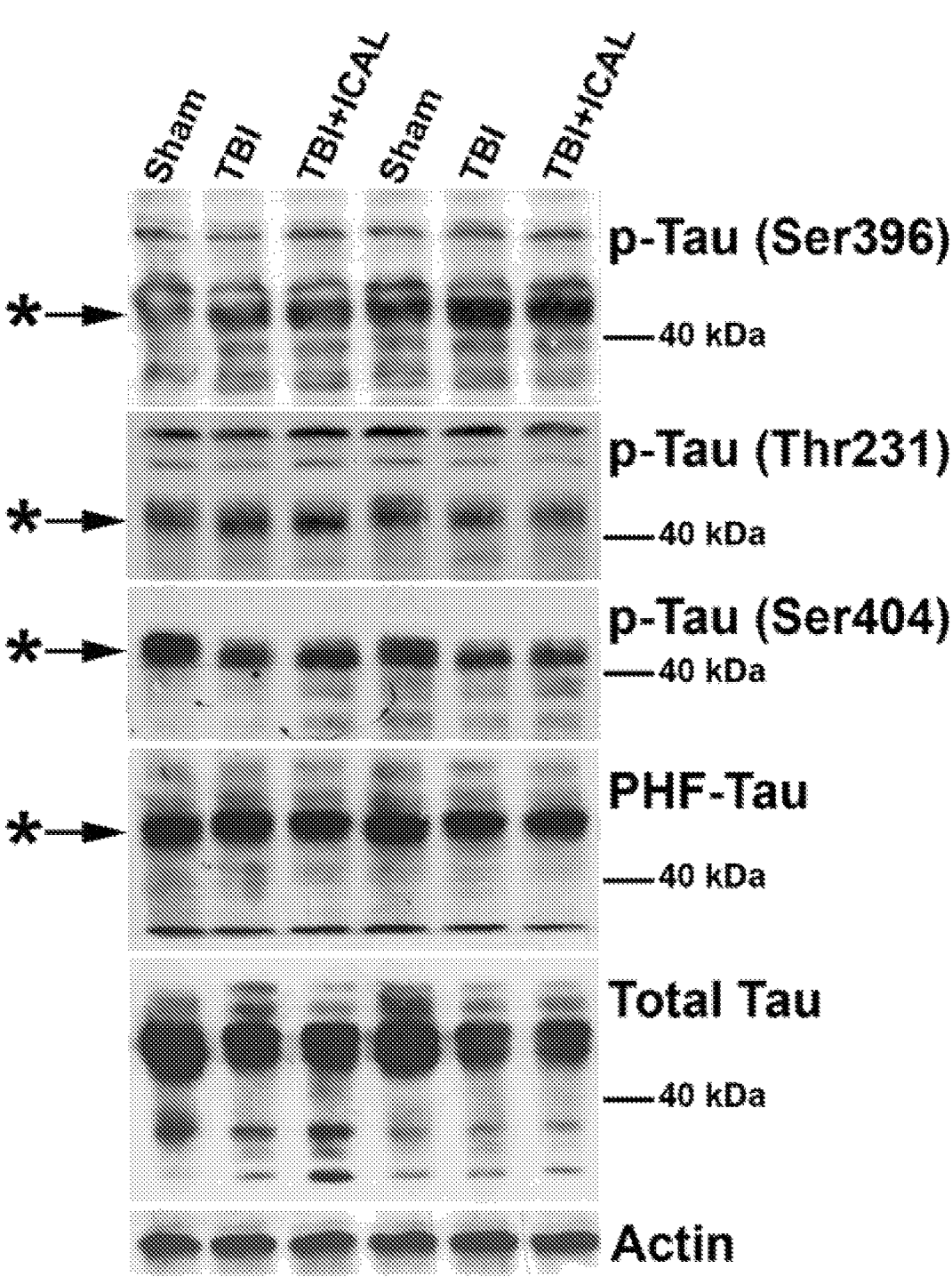
FIG. 2 shows Western blotting for Tau phosphorylation and expression in brain tissue of mice subjected to TBI. At 72 h post-TBI, one half of the brain (excluding cerebellum) was dissected and homogenized in lysis buffer. Whole brain tissue lysates were resolved by SDS-PAGE and proteins transferred to PVDF membranes. A) Blots were sequentially stripped and reprobed with antibodies against Tau phosphorylated on Ser396, Thr231, and Ser404, paired helical filament (PHF) Tau, total Tau, and actin (as a loading control). Asterisks indicate prominent Tau bands and MW markers are shown for estimation of size. The blots shown are from two independent sets of mice (Sham, TBI, TBI+ICAL) which displayed similar results. B) Densitometric analysis of each form of phospho-Tau was performed on three independent sets of mice. Phospho-Tau was normalized to total Tau and this value was set to 1.00 for each Sham mouse; the ratio of phospho-Tau to total Tau was then expressed relative to the Sham control for each set of mice. No statistically significant differences were observed; however, there was a trend towards increased Tau phosphorylation on Ser396 in untreated TBI mice compared to Sham and this trend persisted for TBI mice which had been pretreated with IMMUNOCAL® (one-way ANOVA, p=0.096). Abbreviations used: ICAL, IMMUNOCAL®; p-Tau, phospho-Tau.
Figure 2:
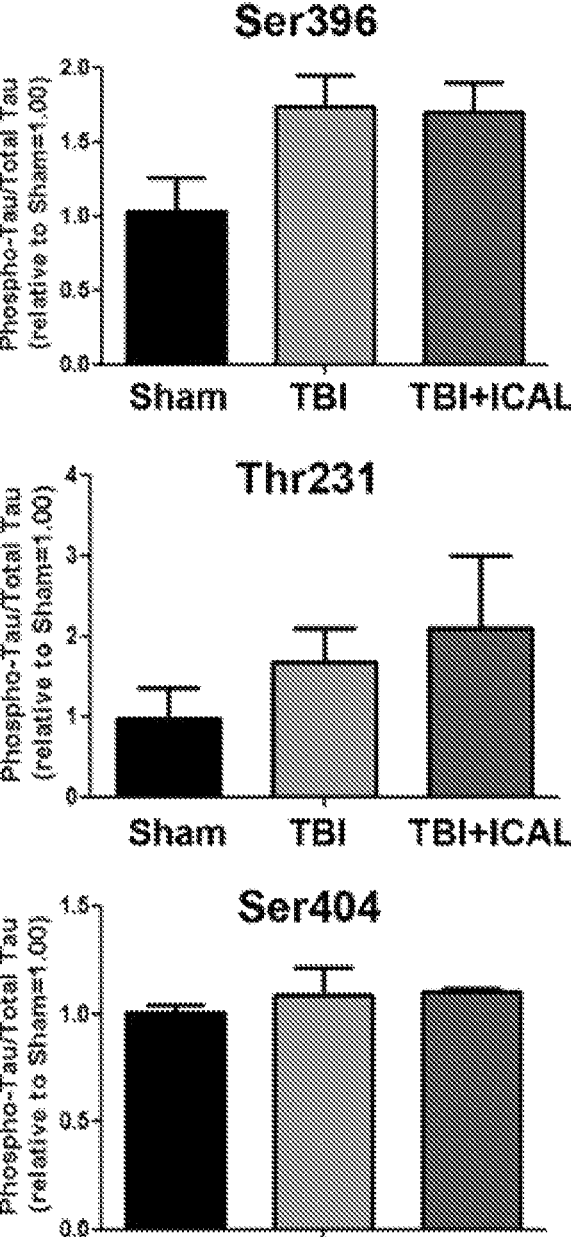

Following MRI analysis, mice were euthanized and brains removed at 72 h post-TBI. One-half of each brain was flash frozen in liquid nitrogen for subsequent HPLC analysis of GSH (discussed below). The other half of the brain was dounce homogenized in lysis buffer and protein samples were resolved by SDS-PAGE and western blotted to assess the phosphorylation status and expression level of the microtubule bundling protein Tau. Several TBI-induced changes in Tau phosphorylation were observed by western blot including an enhanced electrophoretic mobility (downward shift) of Tau phosphorylated on Ser396, Thr231, and Ser404 (FIG. 2). In contrast, TBI induced a decrease in the electrophoretic mobility of Tau recognized by a PHF-Tau antibody. As well, TBI caused a marked reduction in the amount of total Tau observed in brain lysates, while no difference in actin was apparent in the same samples. Finally, quantification of Tau phosphorylated at specific residues and normalized to total Tau revealed no statistically significant increases in Tau phosphorylation at 72 h post-TBI; however, there was a trend towards increased Tau phosphorylation on Ser396 in untreated TBI mice compared to Sham and this trend persisted for TBI mice which had been pretreated with IMMUNOCAL® (FIG. 2B). All of these TBI-induced changes in the electrophoretic mobility of various phospho-Tau forms and the expression of total Tau were observed regardless of whether the samples were obtained from untreated TBI mice or mice pretreated with IMMUNO-CAL® (FIG. 2). In the case of the phospho-Tau bands, only the Ser404 blot shows a clear decrease in the amount of Tau phosphorylated at this site, along with an apparent increase in the electrophoretic mobility of this Tau species. It is unclear precisely what the changes in electrophoretic mobility represent for these various forms of phospho-Tau, but most likely they reflect changes in phosphorylation at other sites on the molecule. Nonetheless, there are detectable changes in Tau phosphorylation and expression induced in this TBI model and they are completely unaffected by pre-injury supplementation with IMMUNOCAL®, suggesting that they may represent biochemical changes caused by or in response to the primary mechanical injury induced by TBI.

Figure 3:
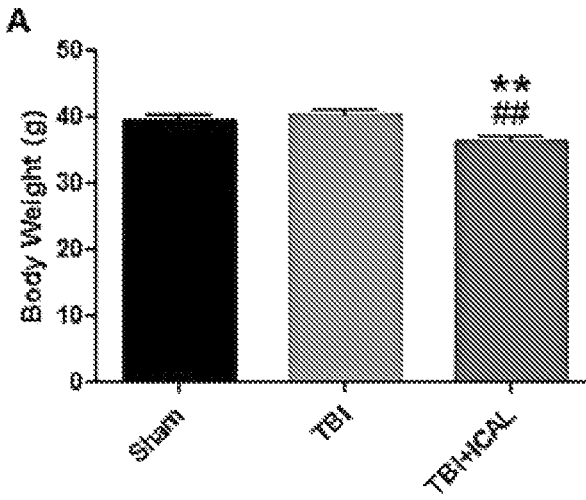
FIG. 3 provides clinical measures following TBI or Sham surgery. A) Body weights (mean±SEM) were assessed on day 0, just prior to TBI or Sham surgery. Mice pretreated for 28 days with IMMUNOCAL® displayed a statistically significant (p<0.01, n=40 mice per group) reduction in body weight compared to both Sham mice () and untreated TBI mice (##). B) Righting reflex times (mean±SEM) were measured immediately post-TBI or Sham surgery. Both untreated and IMMUNOCAL®-pretreated mice subjected to TBI displayed statistically significant (p<0.001, n=40 mice per group) increases in righting reflex times when compared to Sham mice (*). C) Apnea times (mean±SEM) were documented immediately post-TBI or Sham surgery. All of the mice subjected to TBI, including those pretreated with IMMUNOCAL®, displayed substantial periods of apnea following impact, with no significant difference observed between groups (n=20 mice per group; unpaired t-test, p=0.995). By comparison, no mice subjected to Sham surgery displayed any apnea. Abbreviations used: ICAL, IMMUNOCAL®; s, seconds.
Figure 3:
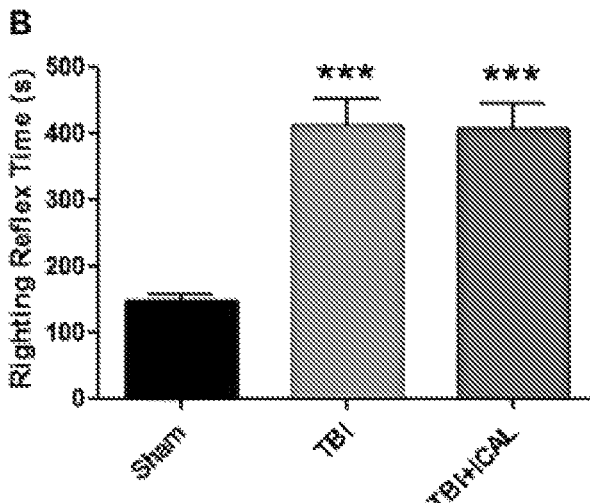
Figure 3:
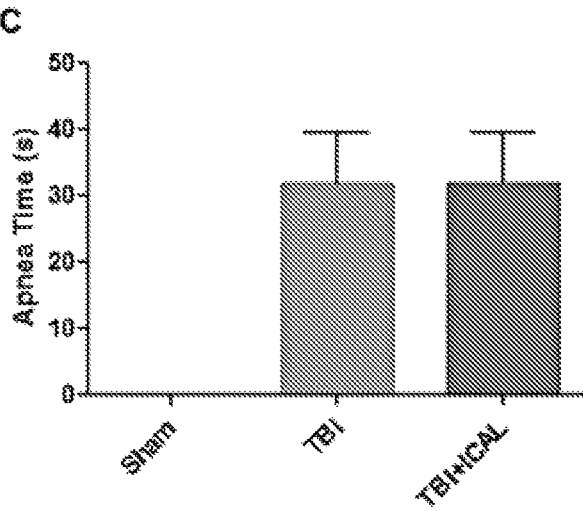

Finally, in addition to the MRI and Tau analyses described above, several clinical indicators also demonstrate that pre-injury supplementation with IMMUNOCAL® did not significantly affect the magnitude of the primary mechanical injury induced by a moderate TBI in mice. IMMUNO-CAL®-pretreated mice had a significantly lower body weight (~10% decrease) than either Sham control mice or untreated TBI mice when weight was assessed just prior to TBI (FIG. 3A). This decrease in body weight may reflect some mild stress due to the 28-day chronic oral dosing procedure or it could represent the animals becoming leaner due to the whey protein administration. TBI induced a statistically significant, nearly three-fold increase in the righting reflex time in comparison to Sham control mice, and this effect was comparable in untreated TBI mice and those pretreated with IMMUNOCAL® (FIG. 3B). In a similar manner, both untreated TBI mice and IMMUNOCAL®-pretreated TBI mice displayed substantial apnea times which were comparable to one another, while Sham control mice did not show any signs of apnea (FIG. 3C). These clinical measures further support the conclusion that pre-injury supplementation with IMMUNOCAL® had no significant effect on the magnitude of the primary brain injury that the mice experienced in response to a moderate TBI.

Figure 4:
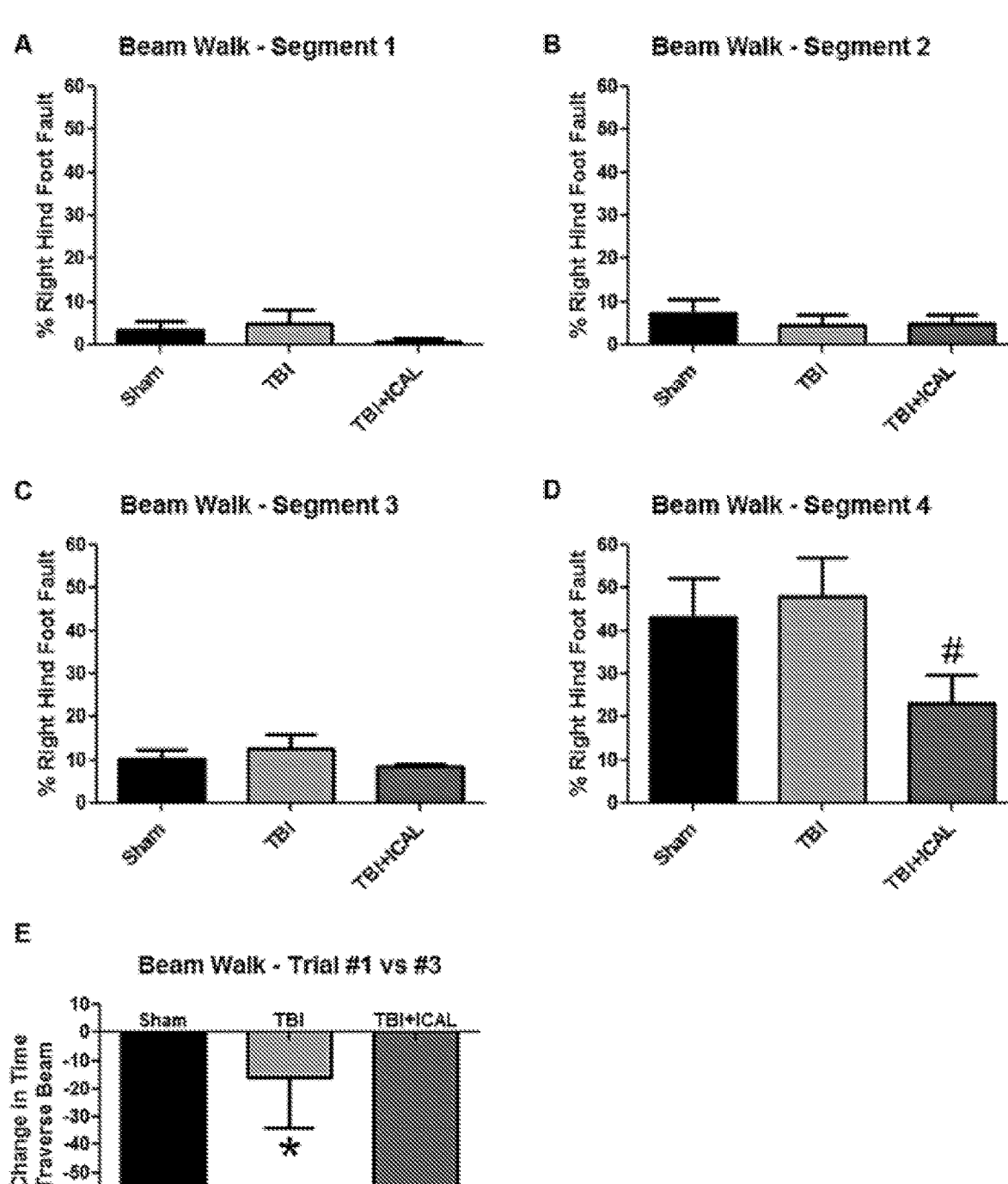
FIG. 4 indicates performance on the challenging beam walk task of mice subjected to TBI. A-D) Percentage of right hind foot faults quantified in narrowing beam segments at 24 h post-TBI. Segments 1~4 represent sections of the beam with progressively narrower widths. All groups showed increasing foot faults as the beam became progressively narrower. In the narrowest section of the beam (section 4), the percentage of right hind foot faults for IMMUNO-CAL®-pretreated mice that were subjected to TBI was statistically significantly lower than the corresponding value for untreated TBI mice (#p<0.05, n=8 mice per group; unpaired t-test; effect size [95% confidence intervals]=−1.10 [−2.09 to 0.00]). E) The percent change in the time taken to traverse the entire beam between trial #1 and trial #3 is shown for each group. Untreated TBI mice showed significantly less improvement than Sham mice (*p<0.05; effect size [95% confidence intervals]=1.53 [0.15 to 2.68]) and IMMUNOCAL®-pretreated mice that were subjected to TBI showed significantly more improvement than untreated TBI mice (#p<0.05, n=6 mice per group; one-way ANOVA, p=0.012; effect size [95% confidence intervals]=−1.42 [−2.55 to −0.06]). Abbreviations used: ICAL, IMMUNO-CAL®.

Pre-Injury Supplementation with IMMUNOCAL® Significantly Improved Motor and Cognitive Deficits Induced by a Moderate TBI Animals were tested for TBI-induced deficits in motor function using the challenging beam walk task and performance on an accelerating rotarod. In the challenging beam walk task, mice were trained prior to TBI to traverse a beam with progressively narrower width segments. On the day of testing (24 h post-TBI), a wire grid was placed over the beam to create a more challenging motor paradigm for the mice. In general, animals in all three groups performed very well on the beam walk with approximately 10% or fewer right hind foot faults observed on the first three beam segments (FIGS. 4A-C). However, on the narrowest width segment of the beam, both Sham control mice and untreated TBI mice had significant difficulty traversing the beam and each group displayed greater than 40% right hind foot faults (FIG. 4D). No significant difference was observed between the Sham control and untreated TBI groups, demonstrating that this effect was not related to TBI but instead reflected the overt difficulty of the task. Notably, IMMUNOCAL®-pretreated mice that were subjected to TBI performed consistently better than either Sham control mice or untreated TBI mice on the narrowest width segment of the beam, though the difference observed was only statistically significant when compared to untreated TBI mice (FIG. 4D).

In addition to assessing right hind foot faults on the beam walk, this motor function test was also utilized as a type of learning paradigm. Because the mice were trained on the beam without the wire grid, addition of this grid on the day of testing represented a new challenge for the mice (i.e., they had to learn to traverse the beam by walking on the wire grid). To assess their capacity to learn this new task, the amount of time taken to traverse the beam on the first of three trials was compared to that on the final of the three trials on the day of testing. Sham control mice clearly learned to traverse the wire grid as evidenced by a nearly 70% reduction in the time taken to traverse the beam between the first and last trial (FIG. 4E). In contrast, untreated TBI mice only improved their time to traverse the beam on average by approximately 20% from the first to the last trial, which was statistically significantly different than the Sham control group. Pre-injury supplementation with IMMUNOCAL® corrected this deficit after TBI and these mice displayed an improvement in time to traverse the beam which was indistinguishable from that of the Sham control group (FIG. 4E).

Figure 5:
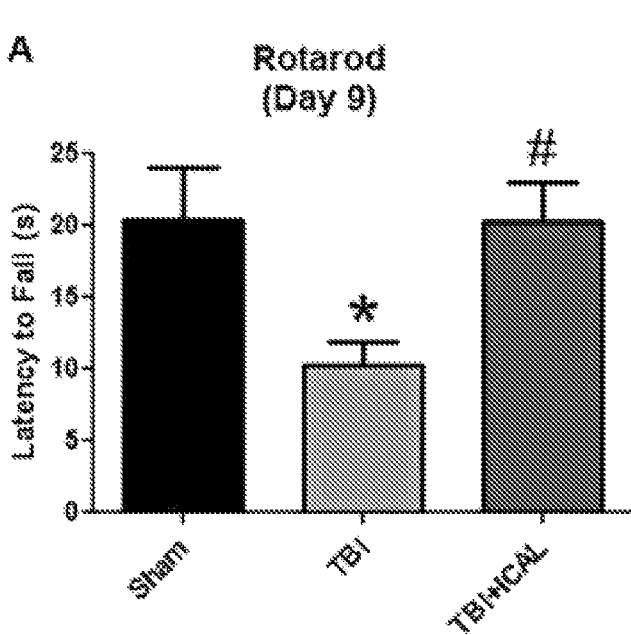
FIG. 5 provides data indicating that pre-injury supplementation with IMMUNOCAL® significantly improved rotarod performance post-TBI. Rotarod performance was assessed on day 9 (A) and day 16 (B) post-TBI. On day 9 post-TBI, time spent on the accelerating rotarod apparatus significantly decreased in untreated TBI mice compared to Sham control mice (*p<0.05; effect size [95% confidence intervals]=−1.40 [−2.46 to −0.15]). This motor deficit was completely prevented by pre-injury supplementation with IMMUNOCAL® (#p<0.05 versus untreated TBI mice, n=7 mice per group; one-way ANOVA, p=0.026; effect size [95% confidence intervals]=1.70 [0.38 to 2.78]). On day 16 post-TBI, no significant differences in latency time were observed between groups (n=6 mice per group; one-way ANOVA, p=0.686). Abbreviations used: ICAL, IMMUNO-CAL®; s, seconds.
Figure 5:
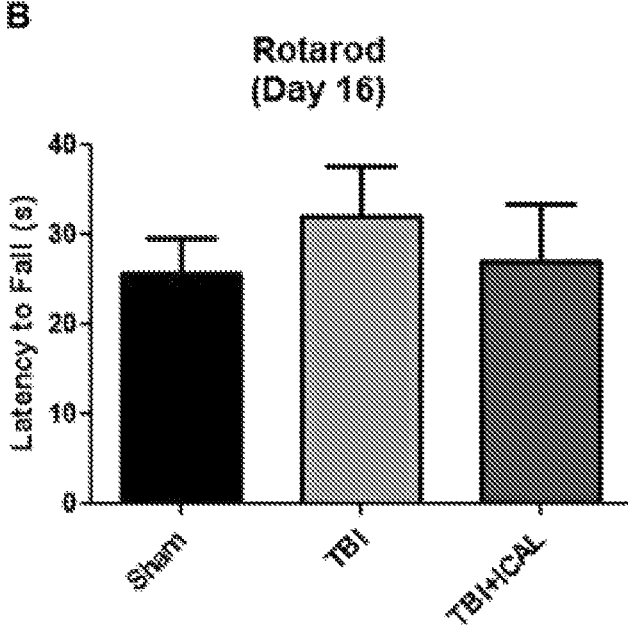

Next, motor performance on an accelerating rotarod at 9 days and 16 days post-TBI was evaluated. On day 9 post-TBI, Sham control mice spent an average of approximately 20 s on the accelerating rotarod before falling off of the apparatus. Untreated TBI mice only remained on the rotating rod for approximately half this time, a statistically significant decrease compared to the Sham control group (FIG. 5A). However, mice pretreated with IMMUNOCAL® prior to TBI showed a latency time to fall which was significantly greater than untreated TBI mice and not statistically different from the Sham control group (FIG. 5A). By day 16 post-TBI, all three groups had increased their performance on the accelerating rotarod and displayed greater latency times to fall than they showed at 9 days post-TBI. In addition, the untreated TBI group appeared to recover their motor function on this task and no longer displayed a significant difference from the Sham control group (FIG. 5B).

Figure 6:
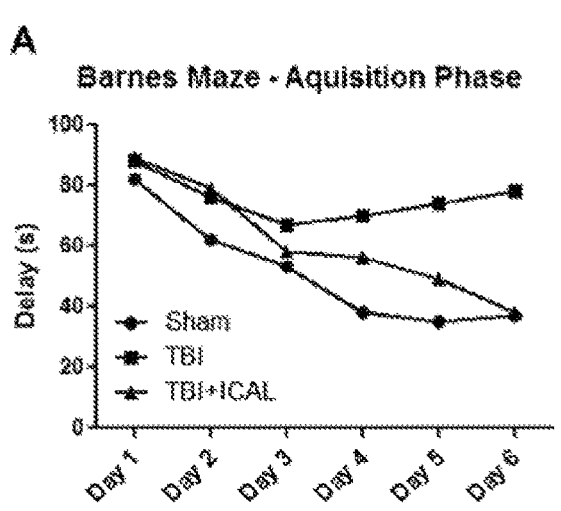
FIG. 6 provides data indicating that pre-injury supplementation with IMMUNOCAL® significantly improved various aspects of Barnes maze performance post-TBI. A) The mean values calculated for the delay time taken to find the escape pod are shown for each group of mice (Sham, TBI, TBI+ICAL) during the six-day acquisition phase of the Barnes maze test (days 10-15 post-TBI). Error bars are not shown in (A) for clarity. Data for day 5 (B) and day 6 (C) of the acquisition phase of the Barnes maze test are shown as the mean±SEM for the delay times observed. B) On day 5, untreated TBI mice displayed a statistically significant increase in delay time to find the escape pod when compared to Sham control mice (*p<0.05, n=4-7 mice per group; one-way ANOVA, p=0.05; effect size [95% confidence intervals]=1.89 [0.43 to 3.09]). C) On day 6, untreated TBI mice displayed a statistically significant increase in delay time to find the escape pod when compared to Sham control mice (** p<0.01, n=6-7 mice per group; one-way ANOVA, p=0.002; effect size [95% confidence intervals]=2.26 [0.88 to 3.39]) and IMMUNOCAL®-pretreated mice that were subjected to TBI showed a statistically significant decrease in delay time in comparison to untreated TBI mice (##p<0.01, n=6-7 mice per group; one-way ANOVA, p=0.002; effect size [95% confidence intervals]=−1.87 [−3.02 to −0.46]). D) Delay times to find the escape pod zone for the probe phase of the Barnes maze test (day 16 post-TBI) are shown as the mean±SEM for each treatment group. The difference between the Sham control group and the untreated TBI group did not quite reach statistical significance (p=0.06; unpaired t-test; effect size [95% confidence intervals]=1.28 [−0.12 to 2.45]). IMMUNOCAL®-pretreated mice that were subjected to TBI showed a statistically significant decrease in delay time in comparison to untreated TBI mice (##p<0.01, n=5-7 mice per group; one-way ANOVA, p=0.009; effect size [95% confidence intervals]=−1.90 [−3.10 to −0.41]). Abbreviations used: ICAL, IMMUNOCAL®; s, seconds.
Figure 6:
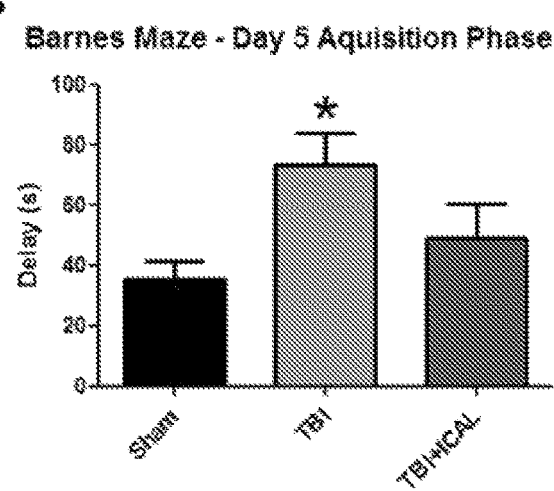
Figure 6:
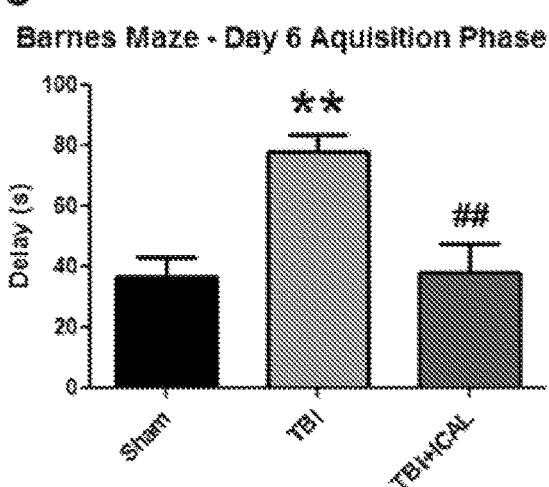
Figure 6:
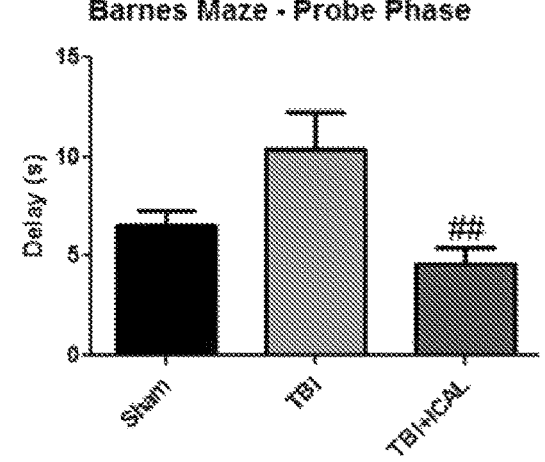

The effects of TBI on cognitive function was also evaluated using the Barnes maze to assess spatial learning and memory on days 10-16 post-TBI. During the six-day acquisition phase of the Barnes maze test, Sham control mice progressively learned to find the escape pod as evidenced by a shortening of the average delay time from approximately 85 s on day 1 compared to less than 40 s on day 6 (FIG. 6A). Over this same time frame, untreated TBI mice appeared to learn less quickly than Sham control mice to find the escape pod and demonstrated a plateau in average delay time of approximately 75 s. IMMUNOCAL®-pretreated mice displayed average delay times that were intermediate between the Sham control group and untreated TBI mice (FIG. 6A). Statistical analysis of the acquisition phase data revealed statistically significant differences between the delay times for the untreated TBI mice and the Sham control group at both day 5 and day 6 (FIGS. 6B and 6C). Furthermore, on day 6 of the acquisition phase, IMMUNOCAL®-pretreated mice that were subjected to TBI showed a statistically significant improvement in delay time to find the escape pod in comparison to untreated TBI mice (FIG. 6C). Finally, in the probe phase of the Barnes maze test, Sham control mice took on average approximately 6 s to find the escape pod zone. Untreated TBI mice took greater than 10 s on average to find the escape pod zone, an effect which was nearly statistically significantly different from the Sham control group (p=0.06). However, mice which had received IMMU-NOCAL® treatment prior to TBI displayed an average delay time of less than 5 s to find the escape pod zone, an effect which was statistically significantly different than untreated TBI mice (FIG. 6D).

Figure 11:
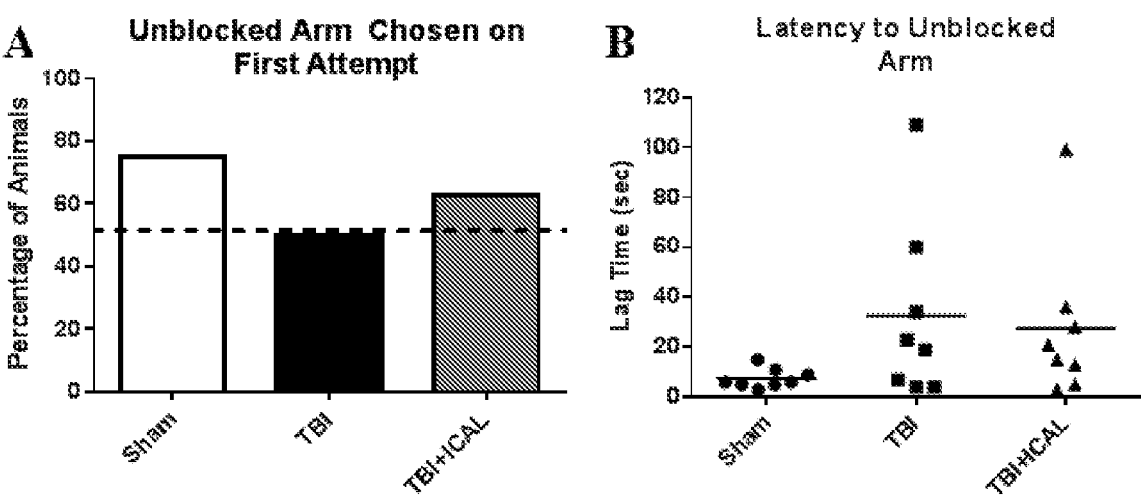
FIG. 11 shows performance in Y-maze trends toward an IMMUNOCAL® mediated effect. (A) The percent of animals that chose the newly unblocked arm on the first attempt decreased in injured animals, but exhibited a noticeable increase in ICAL-treated animals. (B) The lag time to the previously unexplored arm was determined for each individual mouse, with the TBI animals demonstrating an increased average time, and the ICAL-treated animals again showing an intermediate lag time compared to sham and TBI (n=8). Abbreviations used: ICAL, IMMUNOCAL®.

Modified Y-maze testing was also performed, which tests working memory. A clear difference in the lag time (the time it took the animal to enter the previously blocked arm of the maze) between sham and untreated TBI mice was observed (FIG. 11). In general, sham mice very quickly sought to explore the newly opened arm of the maze, whereas TBI animals showed a wide distribution of lag times with some animals taking more than 1 minute to explore the newly opened arm of the maze. Mice pre-treated with IMMUNO-CAL® prior to TBI showed a profile of lag times that were somewhat intermediate (indicating improvement, but still more closely mimicking the untreated TBI mice than sham controls). The percentage of animals that chose the previously blocked arm on the first attempt was determined. If each mouse showed no preference for choosing one arm of the maze over another, then this value should approach 50% or random chance. Sham mice showed a preference for choosing the previously blocked arm with 75% of these animals choosing to enter this arm of the maze on the first attempt (FIG. 11A). Untreated TBI mice chose the previously blocked arm of the maze at a rate equivalent to random chance. IMMUNOCAL® pre-treated mice subjected to TBI chose the previously blocked arm of the maze at an intermediate rate relative to sham and untreated TBI mice.

Figure 7:
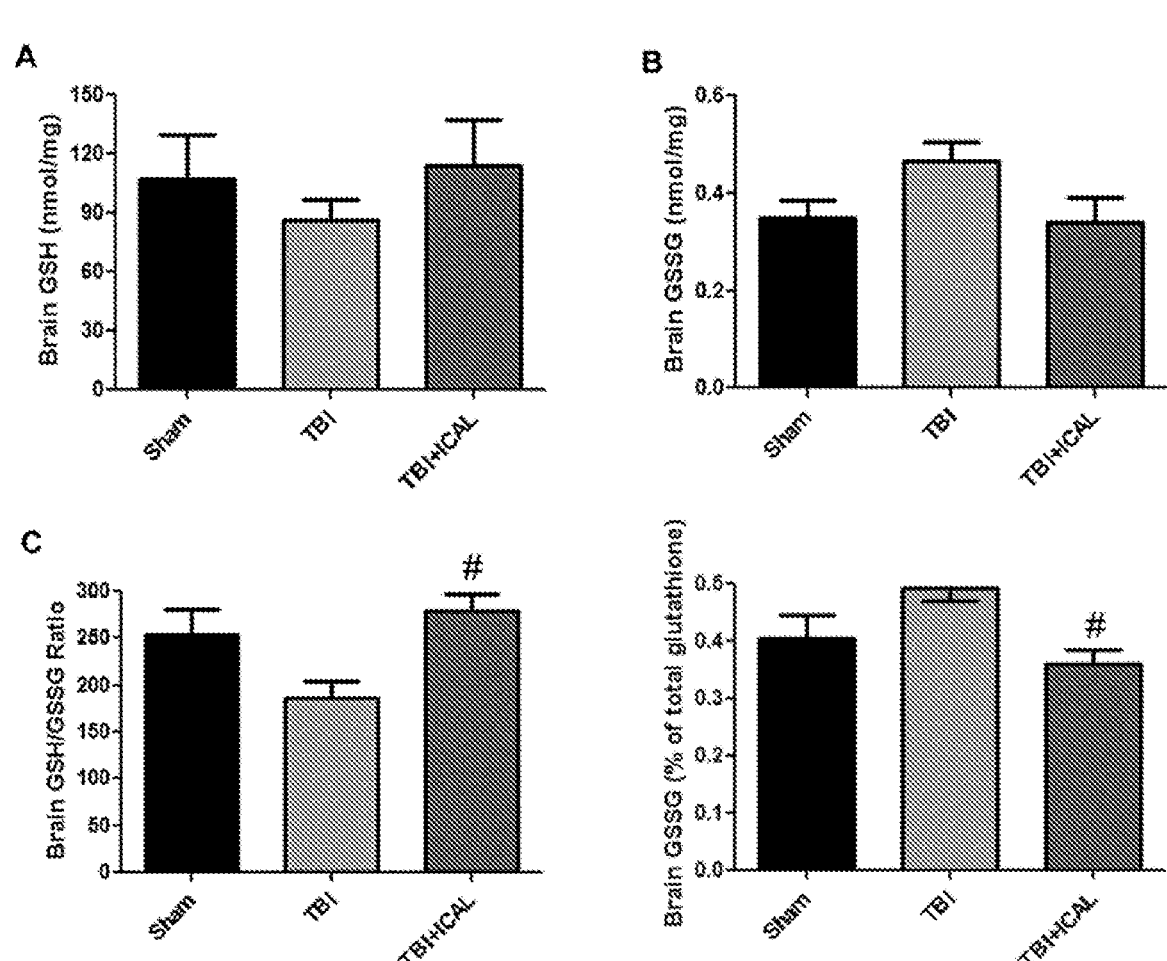
FIG. 7 shows data indicating that pre-injury supplementation with IMMUNOCAL® preserved the brain GSH/GSSG ratio following TBI in mice. At 72 h post-TBI, one half of the brain (excluding cerebellum) was dissected and extracted for analysis of reduced GSH (A) and oxidized GSSG (B) by HPLC with electrochemical detection, as described in the Materials and Methods. No significant differences were observed between groups with respect to total GSH or GSSG, although there was a trend towards enhanced GSSG levels in the untreated TBI group (p=0.09; one-way ANOVA). C) IMMUNOCAL®-pretreated mice that were subjected to TBI showed a statistically significant increase in the GSH/GSSG ratio in comparison to untreated TBI mice (#p<0.05, n=4-6 mice per group; one-way ANOVA, p=0.017; effect size [95% confidence intervals] =2.13 [0.51 to 3.39]). D) IMMUNOCAL®-pretreated mice that were subjected to TBI showed a statistically significant decrease in the % GSSG in comparison to untreated TBI mice (#p<0.05, n=4-5 mice per group; one-way ANOVA, p=0.025; effect size [95% confidence intervals]=−2.17 [−3.46 to −0.45]). Abbreviations used: ICAL, IMMUNO-CAL®.

Pre-Injury Supplementation with IMMUNOCAL® Preserved Brain GSH/GSSG Ratio and Ameliorated Biochemical and Histopathological Indices of Oxidative Damage and Neuronal Injury Induced by a Moderate TBI Several biochemical and histopathological indices of neuronal injury were evaluated in mice subjected to TBI. First, brain levels of GSH and the ratio of reduced GSH to oxidized GSSG at 72 h post-TBI was measured using HPLC with electrochemical detection. The concentrations of GSH and GSSG measured in mouse brain are shown in FIGS. 7A and 7B, respectively. No significant differences were observed between groups with respect to total GSH or GSSG, although there was a trend towards enhanced GSSG levels in the untreated TBI group (FIG. 7B, p=0.09). The ratio of GSH to GSSG was on average, approximately 250 to 1 in the brains of Sham control mice. Untreated TBI mice displayed an approximately 25% reduction in the brain GSH to GSSG ratio in comparison to Sham control mice (FIG. 7C). Pre-injury supplementation with IMMUNOCAL® completely preserved the brain GSH to GSSG ratio measured at 72 h post-TBI at a level significantly higher than that measured in untreated TBI mice and similar to that of the Sham control group (FIG. 7C). Finally, we calculated the amount of GSSG as a percentage of total GSH equivalents (GSH+2 GSSG). The % GSSG trended towards an increase in untreated TBI mice in comparison to Sham control mice, although this change did not reach statistical significance (FIG. 7D, p=0.09). IMMUNOCAL®-pretreated TBI mice displayed a % GSSG in brain which was statistically significantly less than that observed in untreated TBI mice (FIG. 7D).

Figure 12:
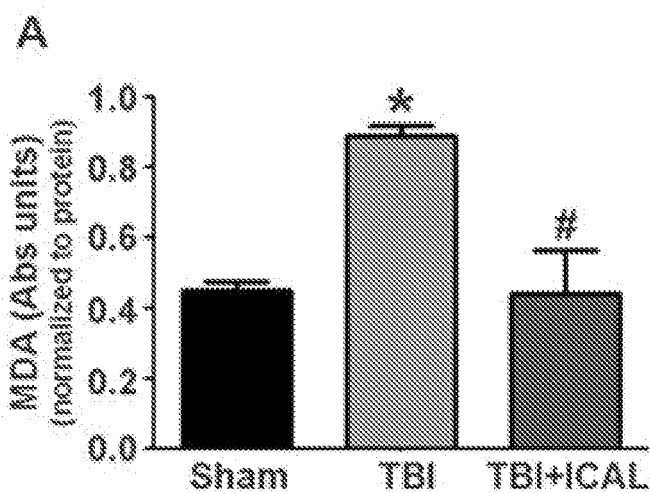
FIG. 12 shows that pre-injury supplementation with IMMUNOCAL® reduced brain lipid peroxidation and preserved BDNF expression following TBI in mice. A) At 72 h post-TBI, one half of the brain (excluding cerebellum) was dissected and homogenized in lysis buffer. Whole brain tissue lysates were assayed for lipid peroxidation using detection of malondialdehyde (MDA) as a marker of oxidative damage. MDA absorbance was normalized to total protein. Untreated TBI mice displayed a statistically significant, approximately two-fold increase in brain MDA content compared to Sham control mice (*p<0.05, n=3-4 mice per group; one-way ANOVA, p=0.012) and IMMUNOCAL®-pretreated mice that were subjected to TBI showed a statistically significant decrease in brain MDA content in comparison to untreated TBI mice (#p<0.05, n=3-4 mice per group; one-way ANOVA, p=0.012). B) Whole brain tissue lysates were resolved by SDS-PAGE and proteins transferred to PVDF membranes. Blots were sequentially stripped and reprobed with antibodies against pro-BDNF/BDNF and Actin. The blots shown are representative of data obtained from three independent sets of mice (Sham, TBI, TBI+ICAL) which displayed similar results. C) Densitometric analysis of pro-BDNF/BDNF expression was performed on three independent sets of mice. Total BDNF (pro-BDNF+BDNF) was normalized to actin and this value was set to 1.00 for each Sham mouse; the ratio of total BDNF to actin was then expressed relative to the Sham control for each set of mice. Untreated TBI mice displayed an approximately 35% reduction in brain BDNF compared to Sham control mice (p<0.05, one-way ANOVA with a post-hoc Dunnett's test). IMMUNOCAL®-pretreated mice that were subjected to TBI showed a statistically significant increase in brain BDNF expression in comparison to untreated TBI mice (##p<0.01, n=3 mice per group; unpaired t-test).
Figure 12:
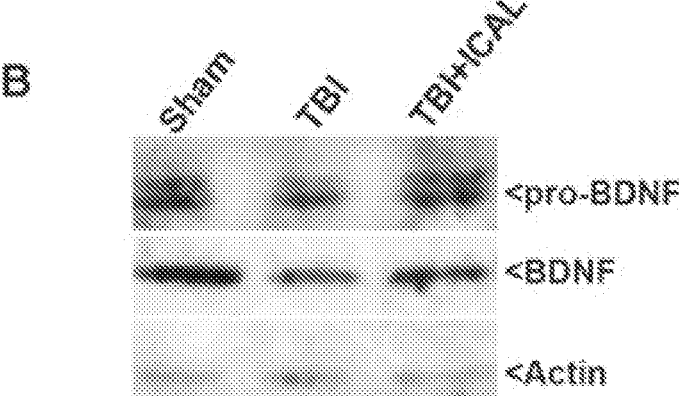
Figure 12:
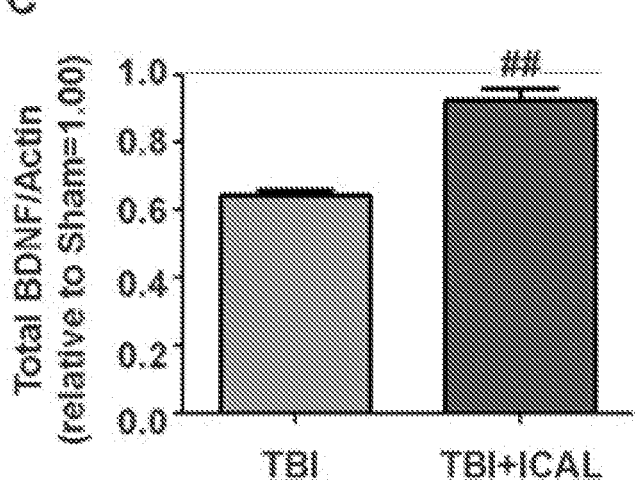

Next, the effects of IMMUNOCAL® pretreatment on lipid peroxidation and expression of brain-derived neurotrophic factor (BDNF) measured at 72 h post-TBI was assessed. Untreated TBI mice displayed a statistically significant, nearly two-fold increase in brain MDA content when compared to Sham control mice and this effect was essentially reversed by pretreatment with IMMUNOCAL® (FIG. 12A). Analysis of brain BDNF expression revealed an approximately 35% decrease in untreated TBI mice compared to Sham control mice at 72 h post-TBI. Pretreatment with IMMUNOCAL® significantly preserved brain BDNF expression at this time point (FIGS. 12B and 12C).

Figure 8:
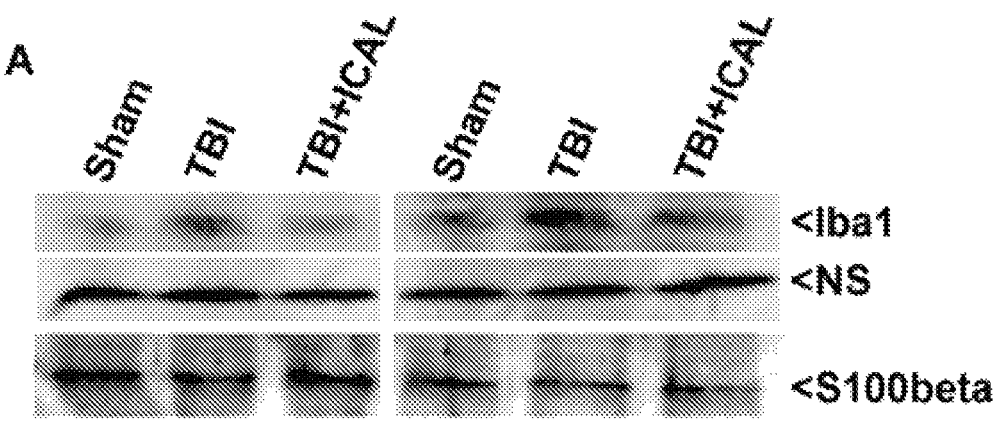
FIG. 8 provides results of assessment of neuroinflammation in mice subjected to TBI. A) At 72 h post-TBI, one half of the brain (excluding cerebellum) was dissected and homogenized in lysis buffer. Whole brain tissue lysates were resolved by SDS-PAGE and proteins transferred to PVDF membranes. Blots were sequentially stripped and reprobed with antibodies against Iba1 (a microglial/macrophage marker), Actin (as a loading control) and S100beta (an astrocyte marker). The blots shown are from two independent sets of mice (Sham, TBI, TBI+ICAL) which displayed similar results. Iba1 levels trended higher in untreated TBI mouse brains than in either the corresponding Sham controls or IMMUNOCAL®-pretreated TBI mouse brains. S100beta levels did not appear to differ substantially between groups. B) Sections of cerebral cortex taken from near the midline and just caudal to bregma were stained for the astrocyte marker GFAP (shown in red) and nuclei were stained with DAPI (shown in blue). Images of 40× fields shown are representative of results observed in multiple sets of mice at 18 days post-TBI. Abbreviations used: ICAL, IMMUNO-CAL®; NS, non-specific band detected by the Iba1 antibody shown as a loading control.
Figure 8:
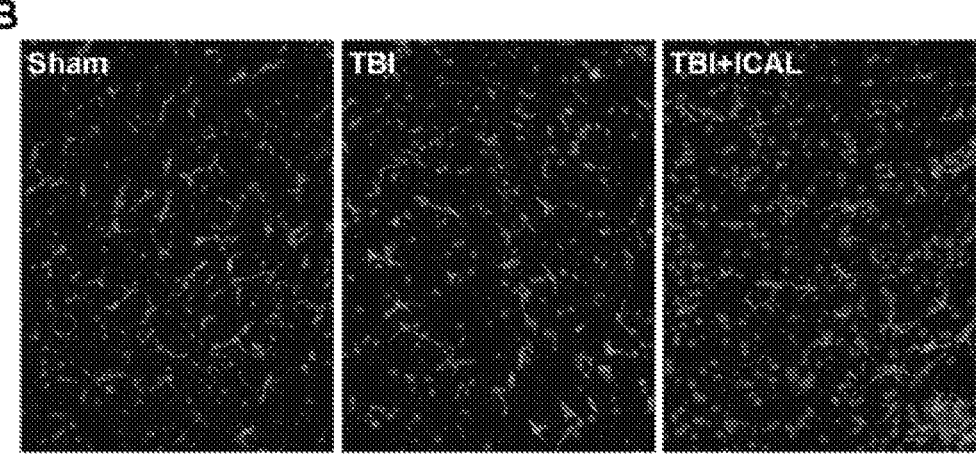

Next, neuroinflammation by western blotting whole brain lysates harvested at 72 h post-TBI for the microglial marker, Iba1, and the astrocyte marker, S100beta was evaluated. In paired sets of mice (i.e., mice which had been subjected to TBI or Sham surgery on the same day), Iba1 immunoreactivity was increased in the brains of untreated TBI mice in comparison to both Sham control mice and IMMUNO-CAL®-pretreated mice subjected to TBI (FIG. 8A). In contrast, no apparent change in immunoreactivity for S100beta was observed in these brain lysates. To further assess reactive astrocytes, we stained for the astrocyte marker, GFAP, in brain sections taken from mice at 18 days post-TBI. No significant differences in the number or morphology of GFAP-positive astrocytes were observed between any of the treatment groups (FIG. 8B).

Figure 9:
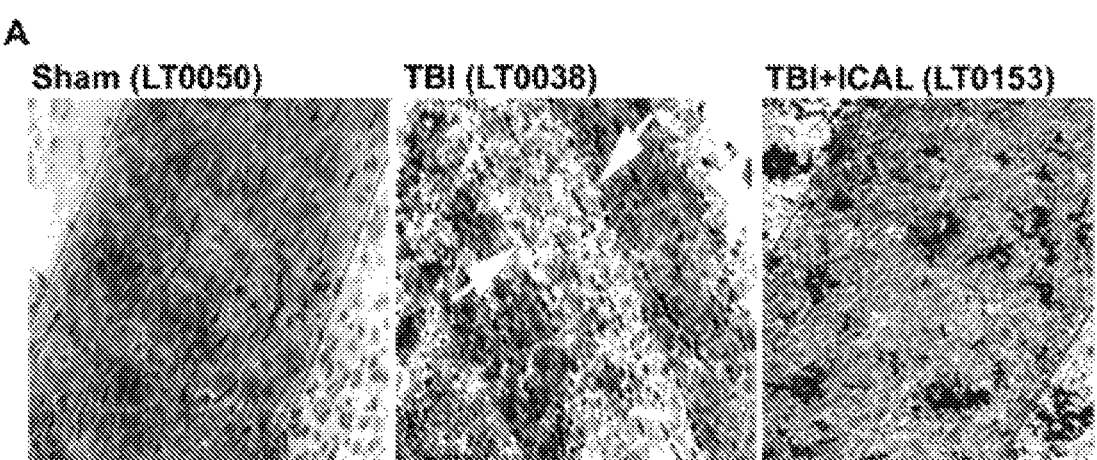
FIG. 9 shows results indicating that pre-injury supplementation with IMMUNOCAL® improved axonal myelination of the corpus callosum in mice subjected to TBI. A) Panels show Luxol fast blue-stained imaging of the mid-body of the corpus callosum at 20× magnification taken at 18 days post-TBI. Red lines indicate maximum width of mid-body and white arrows indicate area of demyelination observed in an untreated TBI mouse. B) Quantification of corpus callosum mid-body measurements. Untreated TBI mice displayed a statistically significant decrease in the maximum width of the corpus callosum mid-body when compared to Sham control mice (*** p<0.001, n=5-7 mice per group; one-way ANOVA, p=0.001; effect size [95% confidence intervals]=−3.40 [−4.84 to −1.44]). IMMUNO-CAL®-pretreated mice that were subjected to TBI showed a statistically significant increase in the maximum width of the corpus callosum mid-body in comparison to untreated TBI mice (#p<0.05, n=5-6 mice per group; one-way ANOVA, p=0.001; effect size [95% confidence intervals] =1.35 [−0.06 to 2.53]). Abbreviations used: ICAL, IMMU-NOCAL®.

Axonal myelination was assessed by staining brain tissue harvested at 18 days post-TBI with Luxol fast blue and measuring the maximal width of the mid-body of the corpus callosum. Sham control mice displayed intact corpus callosum mid-bodies with deep Luxol fast blue staining indicative of extensive axonal myelination (FIG. 9A). Untreated TBI mice displayed either much narrower mid-bodies or corpus callosum with large regions devoid of staining, while IMMUNOCAL®-pretreated mice subjected to TBI showed mostly intact mid-bodies with continuous staining (FIG. 9A). Quantification of the maximum width of the mid-body of the corpus callosum, which stained positively with Luxol fast blue, demonstrated that untreated TBI mice had a statistically significant decrement of approximately 50% in myelinated axons compared to Sham control mice. Pre-injury supplementation with IMMUNOCAL® significantly but only partially, rescued axonal myelination of the corpus callosum following a moderate TBI (FIG. 9B).

Figure 10:
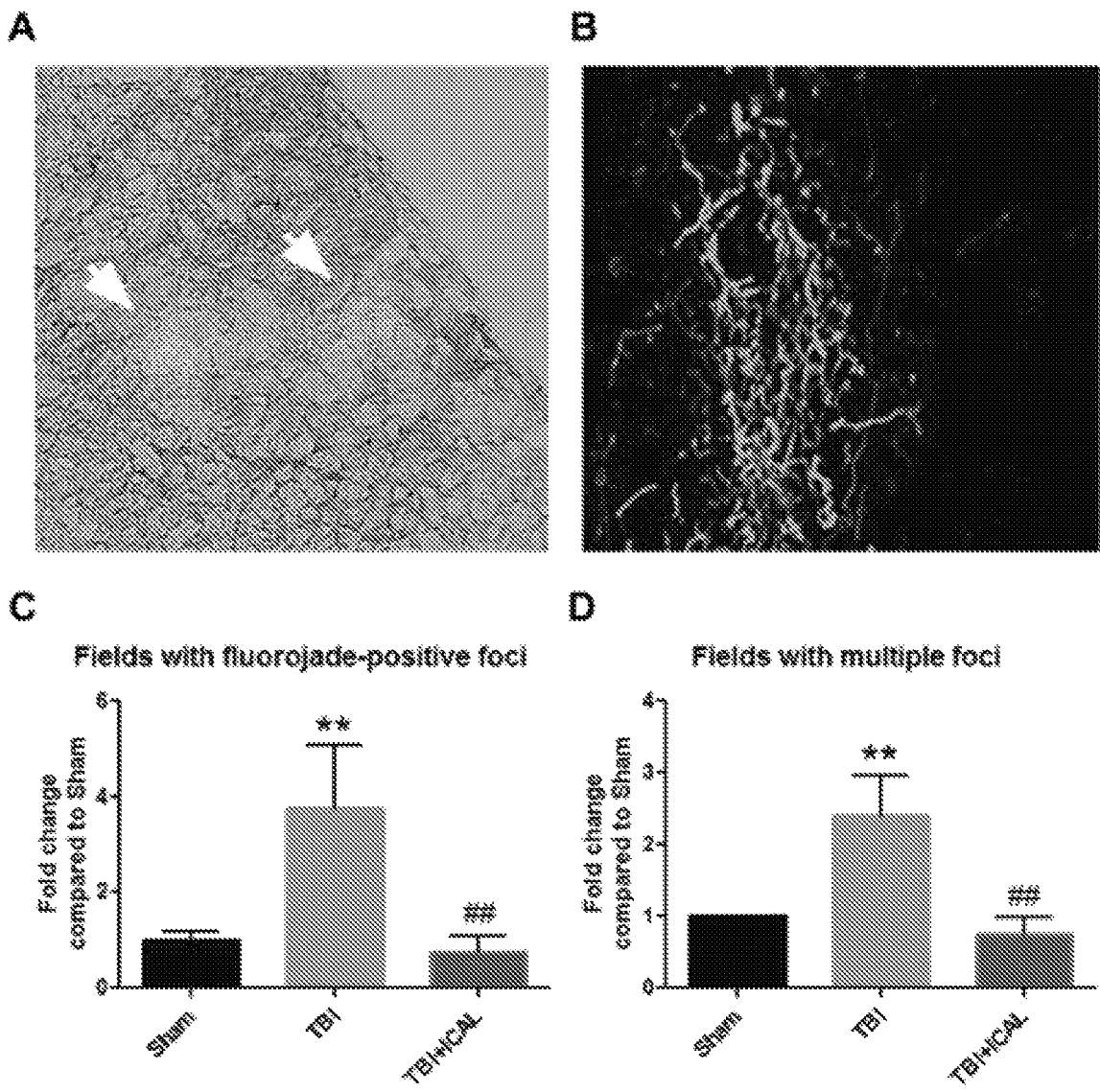
FIG. 10 shows results indicating that pre-injury supplementation with IMMUNOCAL® markedly reduced neuronal degeneration in the brains of mice subjected to TBI. Sections of cerebral cortex taken from near the midline and just caudal to bregma were stained with Fluoro-Jade C to label degenerating neurons at 18 days post-TBI. A) Panel shows an example of two Fluoro-Jade C-positive foci (indicated by the white arrows) in an untreated TBI mouse brain. Foci are shown imposed onto a bright field image of the tissue viewed at 40× magnification. B) An example of a diffuse Fluoro-Jade C-positive foci in an untreated TBI mouse brain. Image magnification increased to show finer detail. C, D) Quantification of the number of 40× fields with a single Fluoro-Jade C-positive foci (or multiple foci) measured as the fold change compared to Sham control mice. Untreated TBI mice displayed statistically significant increases in the number of fields with single (C) and multiple (D) foci when compared to Sham control mice (** p<0.01, n=3-4 mice per group; effect size for single foci [95% confidence intervals]=3.01 [0.73 to 4.50]). IMMUNO-CAL®-pretreated mice that were subjected to TBI showed statistically significant decreases in the number of fields with single (C) and multiple (D) foci in comparison to untreated TBI mice (##p<0.01, n=3-4 mice per group; effect size for single foci [95% confidence intervals]=−3.18 [−4.70 to −0.83]; one-way ANOVA for (C), p=0.007; one-way ANOVA for (D), p=0.004). Abbreviations used: ICAL, IMMUNOCAL®.

Finally, brain tissue harvested at 18 days post-TBI was evaluated for areas of degenerating neurons using Fluoro-Jade C staining. Most Fluoro-Jade C-positive foci were observed in the outer layers of the cerebral cortex, although some isolated regions of staining were also observed in subcortical structures (FIGS. 10A and 10B). Fluoro-Jade C-positive foci were scored across entire coronal sections of brain and the number of 40× fields containing either single or multiple foci were quantified relative to the Sham control group. Untreated TBI mice displayed statistically significant, approximately 4-fold and 2.5-fold increases in the number of fields with single and multiple Fluoro-Jade C-positive foci, respectively, in comparison to the Sham control group (FIGS. 10C and 10D). Pre-injury supplementation with IMMUNOCAL® markedly attenuated neuronal degeneration induced by a moderate TBI, resulting in statistically significant decreases in the numbers of fields with single or multiple Fluoro-Jade C-positive foci in comparison to the untreated TBI group (FIGS. 10C and 10D).

The present studies evaluate the potential of a cysteine-rich, whey protein supplement, IMMUNOCAL®, to enhance resilience to a moderate TBI induced by controlled cortical impact in mice. Untreated CD1 mice subjected to TBI displayed ample evidence of a primary mechanical injury, including regions of brain injury and BBB disruption detected by MRI, alterations in Tau phosphorylation and expression, and substantial increases in righting reflex times and apnea, in comparison to Sham control mice. None of these indices of primary injury were significantly altered by pre-injury supplementation with IMMUNOCAL®. On the other hand, IMMUNOCAL®-pretreated mice subjected to TBI performed significantly better than untreated TBI mice on several aspects of the challenging beam walk task, rotarod performance, and the Barnes maze test, demonstrating marked improvements in these motor and cognitive tasks. Moreover, pre-injury supplementation with IMMU-NOCAL® completely preserved the brain GSH to GSSG ratio in mice subjected to TBI, whereas untreated TBI mice showed a nearly 25% reduction in this ratio which is indicative of oxidative damage. Notably, pre-injury supplementation with IMMUNOCAL® also significantly attenuated lipid peroxidation and preserved BDNF expression in the brain following TBI. Finally, IMMUNOCAL®-pretreated mice subjected to TBI displayed significantly less demyelination of the corpus callosum and reduced numbers of foci of degenerating neurons, when compared to untreated TBI mice. Taken collectively, these results demonstrate that pre-injury supplementation with IMMUNOCAL® significantly increased resilience to a moderate TBI induced by a closed head injury in mice. Thus, the present studies indicate that IMMUNOCAL® may have significant utility as a preventative agent for TBI, particularly in populations at high risk of brain trauma.

As mentioned previously, several studies have reported that brain GSH levels are reduced following TBI and genetic variations in GSH-dependent, peroxide/electrophile-detoxifying enzymes, such as glutathione-S-tranferase-4 and glutathione peroxidase-1, can sensitize mice and rats to brain injury induced by TBI.[25-27] In a similar manner, genetic deletion of the excitatory amino acid carrier type 1 (EAAC1), a glutamate transporter which also participates in the neuronal uptake of cysteine for GSH synthesis, significantly sensitized mice to TBI induced by controlled cortical impact, resulting in enhanced neuronal death and increased microglial activation.[47, 48] A strategy aimed at sustaining or enhancing brain GSH may be a viable approach to mitigate secondary injury processes induced by TBI. In this context, a prior study using a novel closed skull injury model in mice demonstrated that transcranial administration of GSH ameliorated brain injury and neuroinflammation.[49] Moreover, multiple studies have shown that administration of various GSH precursors, including N-acetylcysteine and gamma-glutamylcysteine ethyl ester, as well as the GSH analog, S-nitrosoglutathione, provide antioxidant and neuroprotective effects in mouse and rat models of TBI.[28-33, 50] Most of these previous studies are somewhat limited in scope in that they only evaluated neuronal degeneration and various indices of oxidative or nitrosative stress while neglecting to assess cognitive or motor deficits induced by TBI. As a result, it has been unclear what specific therapeutic benefit such strategy might realistically hold for patients suffering from TBI.

In the present studies, the cysteine-rich, whey protein supplement, IMMUNOCAL®, was observed to not only preserve the brain GSH to GSSG ratio and ameliorate neuronal injury, but it also significantly improved motor and cognitive function in mice tested post-TBI. One previous study using N-acetylcysteine amide also showed a beneficial effect on cognitive function in rats treated post-TBI, as assessed by a modified Morris water maze test.[51] However, motor function was not evaluated in this prior study.

There are a large number of TBI cases which cannot be predicted and therefore, pre-injury administration of a protective therapy is difficult. However, for those individuals in occupations with a high risk of experiencing a TBI, such as military personnel and athletes in contact sports, the present data may be highly relevant. The identification of agents that significantly increase resilience to TBI are highly desirable in the field, since they may provide preventative options to limit the brain injury caused by this type of trauma.

One aspect of the TBI model that was employed in these studies which was unexpected was the relative lack of a large neuroinflammatory response. In particular, we did not observe increases in the reactive astrocyte marker, S100beta, in whole brain lysates assessed by western blotting at 72 h post-TBI. Nor did we observe any notable increases in GFAP immunoreactivity in brain tissue of untreated TBI mice when assayed at 18 days post-TBI. This apparent lack of a global reactive astrogliosis response was not anticipated based on prior studies using a controlled cortical impact paradigm to induce TBI. Although it is interesting to note that Lloyd et al (2008) only showed significant increases in brain S100beta immunoreactivity using this model of moderate TBI induced by controlled cortical impact at 28 days post-TBI.[43] Therefore, it is possible that we simply missed the peak time point of reactive astrogliosis in our assessments at 72 h and 18 days post-TBI. Another possibility is that there were discrete regions of reactive astrogliosis throughout the brains of our untreated TBI mice that we did not identify. During the immunofluorescence imaging of GFAP-stained brain sections, entire coronal sections were evaluated for reactive astrocytes. Although some untreated TBI mice clearly had fields with large numbers of astrocytes, this was also the case for Sham controls and IMMUNO-CAL®-pretreated mice subjected to TBI. In fact, quantitative analysis did not reveal any significant differences between groups in the numbers of GFAP-positive cells per mouse brain section, even when different morphological variants were specifically counted (e.g., ramified versus amoeboid; data not shown). In contrast to the lack of reactive astrocytes, we did observe an increase in Iba1 immunoreactivity in whole brain lysates assessed by western blotting at 72 h post-TBI, an effect which was mitigated by IMMUNOCAL® pretreatment. Interestingly, the present studies found that IMMUNOCAL® suppresses lipopolysaccharide-induced nitric oxide production in cultured BV2 mouse microglial cells, suggesting that this whey protein supplement may possess some anti-neuroinflammatory properties (Khatter and Linseman, unpublished data). Thus, there does seem to be a component of microgliosis in the TBI model that was employed, which was significantly influenced by pretreatment with IMMUNOCAL®.

Without wishing to be bound by theory, our hypothesis as to how might pre-injury administration of IMMUNOCAL® enhance resilience to TBI at the molecular level is based on the observation that pre-injury administration of IMMUNO-CAL® significantly preserved the brain GSH to GSSG ratio in mice subjected to TBI. By preserving brain GSH, IMMU-NOCAL® may mitigate several of the secondary injury mechanisms that are activated by TBI. In this context, we recently demonstrated that IMMUNOCAL® is broadly neuroprotective in vitro and rescues primary cerebellar neurons and various neuronal cell lines from a number of stressors including oxidative damage, nitric oxide, and excitotoxicity.[52] These stressors are believed to contribute to the secondary injury processes post-TBI. Importantly, the neuroprotective effects of IMMUNOCAL® observed in cell culture were dependent on the de novo synthesis of GSH.[52] Thus, it seems probable that at least the neuroprotective actions of IMMUNOCAL® observed in this mouse model of TBI may be due largely to its capacity to act as a cysteine delivery system and thereby, a precursor pool for GSH synthesis. Downstream of preserving GSH, pre-injury supplementation with IMMUNOCAL® significantly attenuated lipid peroxidation and preserved BDNF expression in the brain following TBI. Similar effects on BDNF expression have previously been observed in rat models of controlled cortical impact injury with procyanidin antioxidants and S-nitrosoglutathione (Khan et al., 2011; Mao et al., 2015). Collectively, these findings suggest that the neuroprotective mechanism of action of IMMUNOCAL® in TBI may stem from its capacity to preserve GSH and in turn, to limit oxidative damage and maintain neurotrophic factors.

In summary, pre-injury oral administration of the cysteine-rich, whey protein supplement, IMMUNOCAL®, significantly enhanced resilience to TBI induced by controlled cortical impact in the mice of these studies. Although IMMUNOCAL® did not protect mice from the primary mechanical injury induced by a moderate TBI, it did preserve the brain GSH to GSSG ratio, reduce lipid peroxidation, sustain BDNF expression, and attenuate demyelination and neuronal degeneration. The therapeutic actions of IMMUNOCAL® pretreatment were evidenced by significant improvements in motor and cognitive deficits induced by TBI. These experimental results indicate that IMMUNO-CAL® may provide a particularly interesting preventative agent for TBI-induced damage, particularly in those individuals at high risk of such injury.

Example 2—Whey Characteristics of Whey Protein Isolate Production

An example of whey protein isolate production is provided below for illustrative purposes intended for the person of skill in the art.

As will be understood, whey may be considered as a by-product of cheese or of casein manufacture. Whey typically contains soluble proteins of milk, so-called whey proteins. Cheese whey, for example, typically contains 5-8 g/l of proteins (N×6.38), among which β-lactoglobulin (β-lg) and a-lactalbumin (α-la) are the most abundant (accounting for 50-55% and 15-20% of total whey proteins, respectively) and bovine serum albumin (BSA), lactoferrin (LF) and immunoglobulins (IgG) are considered as minor whey proteins (accounting each for 3-5%). Whey may also comprise protein fragments or polypeptides such as so-called proteose-peptones (PP-4, PP-5, PP-8f) resulting from proteolysis of milk proteins by lactic starters in cheesemaking or by psychotropic bacteria during cold storage of raw milk. These proteinaceous compounds are not completely characterized, and their concentration in whey is highly variable. Finally, non-protein nitrogen (NPN) group may comprise a large number of molecules in whey, among which urea may account for 50-60%.

For illustrative purposes, Table 1 below provides some characteristics of some of the major proteins and polypeptides found in an exemplary whey sample (in this case, bovine sweet whey).

TABLE 1

Some Characteristics of Major Proteins and Polypeptides in an Exemplary Whey Sample

| Protein or polypeptide | Weight contribution (g/l) (approx.) | Molecular weight |
|---|---|---|
| β-lactoglobulin | 3.0 | 18 400 |
| α-lactalbumin | 1.2 | 14 200 |
| BSA | 0.3 | 69 000 |
| Lactoferrin | 0.2 | 77 000 |
| IgG | 0.2 | 160 000 |
| PP-3 | 0.6 | 22 000 |
| PP-5 | | 14 300 |
| PP-8f | | 4 100 |
| NPN | 1.6 | |

In this example, whey protein isolate may be obtained from whey, such as the whey exemplified above in Table 1. As will be understood, process steps involved in the manufacture of whey protein isolate (WPI) may lead to compositional differences in terms of protein profile between whey protein isolates. Thus, the specific components and their abundance are not meant to be considered limiting in any manner. Factors influencing whey protein isolate characteristics may include, for example:

[1] Source of the whey proteins: For example, sweet- or acid-whey may be used as starting material for the manufacture of WPI;

[2] Pasteurization: For example, the proteins in cheese whey-derived ingredients may be submitted to two (2) pasteurization (i.e. 72-75° C.-12-16 sec.) treatments at a cheese plant where milk is pasteurized (Canada and US regulation) before cheesemaking, or at the ingredient manufacturing plant, or before transportation of drained whey to this plant, in order to reduce bacterial count before membrane processing or ion exchange chromatography; and

[3] Defatting: For example, centrifugal clarification is typically used to reduce the fat content of whey to 0.8-1.2%. However, an additional defatting step is often performed to further decrease the fat content to 0.3-0.5% in order to increase membrane separation performance or to prevent an irreversible fouling or clugging of ion-exchange resins with polar lipids. Defatting typically involves holding whey at 50-55° C. for 30 to 90 min. in order to promote aggregation of fat particles (optionally in the presence of added CaCl2). The product will thereafter be submitted to centrifugal separation or MF in order to remove the agglomerated material.

In this example, high-protein concentration (>90% dry basis) whey protein isolate may typically be prepared from whey such as that exemplified in Table 1 by either of two methods: membrane processing or ion-exchange chromatography. In membrane processing, microfiltration (MF) and/or ultrafiltration (UF) membranes may be used for concentrating whey. In ion-exchange chromatography, cationic- and/or anionic-exchange chromatography may be used to purify whey proteins.

In this example, obtained samples may be submitted to spray drying conditions. Where a substantially undenatured isolate is to be prepared, the obtained concentrated liquid may be, for example, sprayed in a hot air current (inlet T°: 180-200° C., outlet T°: 80-100° C.) circulating in a spray drying tower. A combination of dehydration and gravity may allow the collection of dry particles (4-8% humidity) at the bottom of the spray dryer. Estimates obtained from mathematical modeling of such drying processes suggest that the droplet temperature does not exceed about 80-85° C. during the few seconds used for dehydration, providing for an example of low impact spray drying which may not substantially denature whey protein.

As will be understood, ingredients having high-protein contents may generally be more difficult to rehydrate (possibly because of their low lactose and minerals content). For certain applications where rapid rehydration of the powder obtained from spray drying is desired, the powder may be submitted to agglomeration. Such steps may involve a final drying of the powder (from 12-15% to 4% humidity) on a fluid bed, generating agglomerated particles having better sinkability in water. In products containing fat (which is generally not the case for high protein ingredients), lecithin may be injected during fluid bed drying. Lecithin may cover fat droplets and improve their wettability. Instantization step(s) may also be used, although such steps are generally uncommon in the manufacture of high-protein ingredients.

As a result of the above steps, an example of a whey protein isolate may be prepared from the whey protein starting material exemplified in Table 1 above. It will be understood that this example is provided for illustrative and non-limiting purposes, and that many alternative, substituted, or modified whey protein sources and/or processing steps known to the person of skill in the art having regard to the teachings herein are also contemplated.

One or more illustrative embodiments have been described by way of example. It will be understood to persons skilled in the art that a number of variations and modifications can be made without departing from the scope of the invention as defined in the claims.

REFERENCES

1. Masel, B. E., and DeWitt, D. S. (2010). Traumatic brain injury: a disease process, not an event. J. Neurotrauma 27, 1529-1540.
2. Faul, M., Xu, L., Wald, M. M., and Coronado, V. G. (2010). Traumatic brain injury in the United States: emergency department visits, hospitalizations, and deaths. Atlanta (GA): Center for Disease Control and Prevention, National Center for Injury Prevention and Control.

3. Blennow, K., Hardy, J., and Zetterberg, H. (2012). The neuropathology and neurobiology of traumatic brain injury. Neuron 76, 886-899.
4. Baugh, C. M., Stamm, J. M., Riley, D. O., Gavett, B. E., Shenton, M. E., Lin, A., Nowinski, C. J., Cantu, R. C., McKee, A. C., and Stern, R. A. (2012). Chronic traumatic encephalopathy: neurodegeneration following repetitive concussive and subconcussive brain trauma. Brain Imaging Behav 6, 244-254.
5. Guskiewicz, K. M., Marshall, S. W., Bailes, J., McCrea, M., Cantu, R. C., Randolph, C., and Jordan, B. D. (2005). Association between recurrent concussion and late-life cognitive impairment in retired professional football players. Neurosurgery 57, 719-726.
6. McKee, A. C., Cantu, R. C., Nowinski, C. J., Hedley-Whyte, E. T., Gavett, B. E., Budson, A. E., Santini, V. E., Lee, H. S., Kubilus, C. A., and Stern, R. A. (2009). Chronic traumatic encephalopathy in athletes: progressive tauopathy after repetitive head injury. J Neuropathol Exp Neurol 68, 709-735.
7. Broglio, S. P., Eckner, J. T., Martini, D., Sosnoff, J. J., Kutcher, J. S., and Randolph, C. (2011). Cumulative head impact burden in high school football. J Neurotrauma 28, 2069-2078.
8. Gavett, B. E., Stern, R. A., and McKee, A. C. (2011). Chronic traumatic encephalopathy: a potential late effect of sportrelated concussive and subconcussive head trauma. Clin Sports Med 30, 179-188.
9. Elder, G. A., and Cristian, A. (2009). Blast-related mild traumatic brain injury: mechanisms of injury and impact on clinical care. Mt Sinai J Med 76, 111-118.
10. Goldstein, L. E., Fisher, A. M., Tagge, C. A., Zhang, X. L., Velisek, L., Sullivan, J. A., Upreti, C., Kracht, J. M., Ericsson, M., Wojnarowicz, M. W., Goletiani, C. J., Maglakelidze, G. M., Casey, N., Moncaster, J. A., Minaeva, O., Moir, R. D., Nowinski, C. J., Stern, R. A., Cantu, R. C., Geiling, J., Blusztajn, J. K., Wolozin, B. L., Ikezu, T., Stein, T. D., Budson, A. E., Kowall, N. W., Chargin, D., Sharon, A., Saman, S., Hall, G. F., Moss, W. C., Cleveland, R. O., Tanzi, R. E., Stanton, P. K., and McKee, A. C. (2012). Chronic traumatic encephalopathy in blast-exposed military veterans and a blast neurotrauma mouse model. Sci Transl Med 4, 134-160.
11. Gavett, B. E., Stern, R. A., Cantu, R. C., Nowinski, C. J., and McKee, A. C. (2010). Mild traumatic brain injury: a risk factor for neurodegeneration. Alzheimers Res Ther 2, 18.
12. Johnson, V. E., Stewart, W., and Smith D. H. (2010). Traumatic brain injury and amyloid-beta pathology: a link to Alzheimer's disease? Nat Rev Neurosci 11, 361-370.
13. Shively, S., Scher, A. I., Perl, D. P., and Diaz-Arrastia, R. (2012). Dementia resulting from traumatic brain injury: what is the pathology? Arch Neurol 69, 1245-1251.
14. Lee, Y. K., Hou, S. W., Lee, C. C., Hsu, C. Y., Huang, Y. S., and Su, Y. C. (2013). Increased risk of dementia in patients with mild traumatic brain injury: a nationwide cohort study. PLOS One 8, e62422.
15. Garnder, R. C., and Yaffe, K. (2015). Epidemiology of mild traumatic brain injury and neurodegenerative disease. Mol Cell Neurosci 66, 75-80.
16. Hall, E. D., Vaishnav, R. A., and Mustafa, A. G. (2010). Antioxidant therapies for traumatic brain injury. Neurotherapeutics 7, 51-61.
17. Xiong, Y., Mahmood, A., and Chopp, M. (2010). Neurorestorative treatments for traumatic brain injury. Discov Med 10, 434-442.

18. Lulic, D., Burns, J., Bae, E. C., van Loveren, H., and Borlongan, C. V. (2011). A review of laboratory and clinical data supporting the safety and efficacy of cyclosporin A in traumatic brain injury. Neurosurgery 68, 1172-1185.

19. Kumar, A., and Loane, D. J. (2012). Neuroinflammation after traumatic brain injury: opportunities for therapeutic intervention. Brain Behav Immun 26, 1191-1201.

20. McConeghy, K. W, Hatton, J., Hughes L., and Cook, A. M. (2012). A review of neuroprotection pharmacology and therapies in patients with acute traumatic brain injury. CNS Drugs 26, 613-636.

21. Gruenbaum, S. E., Zlotnik, A., Gruenbaum, B. F., Hersey, D., and Bilotta, F. (2016). Pharmacologic neuroprotection for functional outcomes after traumatic brain injury: a systematic review of the clinical literature. CNS Drugs 30, 791-806.

22. Simon, D. W., McGeachy, M. J., Bayir, H., Clark, R. S., Loane, D. J., and Kochanek, P. M. (2017). The far-reaching scope of neuroinflammation after traumatic brain injury. Nat Rev Neurol 13, 171-191.

23. Bains, M., and Hall, E. D. (2012). Antioxidant therapies in traumatic brain and spinal cord injury. Biochim Biophys Acta 1822, 675-684.

24. Abdul-Muneer, P. M., Chandra, N., and Haorah, J. (2015). Interactions of oxidative stress and neurovascular inflammation in the pathogenesis of traumatic brain injury. Mol Neurobiol 51, 966-979.

25. Tyurin, V. A., Tyurina, Y. Y., Borisenko, G. G., Sokolova, T. V., Ritov, V. B., Quinn, P. J., Rose, M., Kochanek, P., Graham, S. H., and Kagan, V. E. (2000). Oxidative stress following traumatic brain injury in rats: Quantitation of biomarkers and detection of free radical intermediates. J Neurochem 75, 2178-2189.

26. Al Nimer, F., Strom, M., Lindblom, R., Aeinehband, S., Bellander, B. M., Nyengaard, J. R., Lidman, O., and Piehl, F. (2013). Naturally occurring variation in the gluta-thione-s-transferase 4 gene determines neurodegeneration after traumatic brain injury. Antioxid Redox Signal 18, 784-794.

27. Xiong, Y., Shie, F. S., Zhang, J., Lee, C. P., and Ho, Y. S. (2004). The protective role of cellular glutathione peroxidase against trauma-induced mitochondrial dysfunction in the mouse brain. J Stroke Cerebrovasc Dis 13, 129-137.

28. Xiong, Y., Peterson, P. L., and Lee, C. P. (1999). Effect of N-acetylcysteine on mitochondrial function following traumatic brain injury in rats. J Neurotrauma 16, 1067-1082.

29. Hicdonmez, T., Kanter, M., Tiryaki, M., Parsak, T., and Cobanoglu, S. (2006). Neuroprotective effects of N-ace-tylcysteine on experimental closed head trauma in rats. Neurochem Res 31, 473-481.

30. Reed, T. T., Owen, J., Pierce, W. M., Sebastian, A., Sullivan, P. G., and Butterfield, D. A. (2009). Proteomic identification of nitrated brain proteins in traumatic brain-injured rats treated postinjury with gamma-glutamylcys-teine ethyl ester: insights into the role of elevation of glutathione as a potential therapeutic strategy for traumatic brain injury. J Neurosci Res 87, 408-417.

31. Lok, J., Leung, W., Zhao, S., Pallast, S., van Leyen, K., Guo, S., Wang, X., Yalcin, A., and Lo, E. H. (2011). Gammaglutamylcysteine ethyl ester protects cerebral endothelial cells during injury and decreases blood-brain barrier permeability after experimental brain trauma. J Neurochem 118, 248-255.

32. Khan, M., Im, Y. B., Shunmugavel, A., Gilg, A. G., Dhindsa, R. K., Singh, A. K., and Singh, I. (2009). Administration of Snitrosoglutathione after traumatic brain injury protects the neurovascular unit and reduces secondary injury in a rat model of controlled cortical impact. J Neuroinflammation 6, 32.

33. Khan, M., Sakakima, H., Dhammu, T. S., Shunmugavel, A., Im, Y. B., Gilg, A. G., Singh, A. K., and Singh, I. (2011). S-nitrosoglutathione reduces oxidative injury and promotes mechanisms of neurorepair following traumatic brain injury in rats. J Neuroinflammation 8, 78.

34. Tateishi, N., Higashi, T., Shinya, S., Naruse, A., and Sakamoto, Y. (1974). Studies on the regulation of gluta-thione level in rat liver. J Biochem 75, 93-103.

35. Meister, A. (1984). New aspects of glutathione biochemistry and transport-selective alteration of glutathione metabolism. Nutr Rev 42, 397-410.

36. Bounous, G., and Gold, P. (1991). The biological activity of undenatured dietary whey proteins: role of glutathione. Clin Invest Med 14, 296-309.

37. Bounous, G., and Kongshavn, P. A. (1978). The effect of dietary amino acids on immune reactivity. Immunology 35, 257-266.

38. Bounous, G., Baruchel, S., Falutz, J., and Gold, P. (1993). Whey proteins as a food supplement in HIV-seropositive individuals. Clin Invest Med 16, 204-209.

39. Grey, V., Mohammed, S. R., Smountas, A. A., Bahlool, R., and Lands, L. C. (2003). Improved glutathione status in young adult patients with cystic fibrosis supplemented with whey protein. J Cyst Fibros 2, 195-198.

40. Physicians' Desk Reference (PDR). (2016). PDR Network (Montvale, NJ); 70th 2016 ed.

41. Ross, E. K., Winter, A. N., Wilkins, H. M., Sumner, W. A., Duval, N., Patterson, D., and Linseman, D. A. (2014). A cystine-rich whey supplement (IMMUNOCAL (®)) delays disease onset and prevents spinal cord glutathione depletion in the hSOD1 (G93A) mouse model of amyotrophic lateral sclerosis. Antioxidants 3, 843-865.

42. Song, W., Tavitian, A., Cressatti, M., Galindez, C., Liberman, A., and Schipper, H. M. (2017). Cysteine-rich whey protein isolate (IMMUNOCAL (®)) ameliorates deficits in the GFAP.HMOX1 mouse model of schizophrenia. Free Radic Biol Med 110, 162-175.

43. Lloyd, E., Somera-Molina, K., Van Eldik, L. J., Watterson, D. M., and Wainwright, M. S. (2008). Suppression of acute proinflammatory cytokine and chemokine upregulation by post-injury administration of a novel small molecule improves long-term neurologic outcome in a mouse model of traumatic brain injury. J Neuroinflammation 5, 28.

44. Fleming, S. M., Ekhator, O. R., and Ghisays, V. (2013). Assessment of sensorimotor function in mouse models of Parkinson's disease. J Vis Exp 76, e50303.

45. Mouzon, B., Chaytow, H., Crynen, G., Bachmeier, C., Stewart, J., Mullan, M., Stewart, W., and Crawford, F. (2012). Repetitive mild traumatic brain injury in a mouse model produces learning and memory deficits accompanied by histological changes. J Neurotraum 29, 2761-2773.

46. Frey, L., Lepkin, A., Schickedanz, A., Huber, K., Brown, M. S., and Serkova. N. (2014). ADC mapping and T1-weighted signal changes on post-injury MRI predict seizure susceptibility after experimental traumatic brain injury. Neurol Res 36, 26-37.

47. Aoyama, K., Suh, S. W., Hamby, A. M., Liu, J., Chan, W. Y., Chen, Y., and Swanson, R. A. (2006). Neuronal

33 glutathione deficiency and age-dependent neurodegeneration in the EAAC1 deficient mouse. Nat Neurosci 9, 119-126.

48. Choi, B. Y., Kim, I. Y., Lee, B. H., Lee, S. H., Kho, A. R., Jung, H. J., Sohn, M., Song, H. K., and Suh, S. W. (2016). Decreased cysteine uptake by EAAC1 gene deletion exacerbates neuronal oxidative stress and neuronal death after traumatic brain injury. Amino Acids 48, 1619-1629.

49. Roth, T. L., Nayak, D., Atanasijevic, T., Koretsky, A. P., Latour, L. L., and McGavern, D. B. (2014). Transcranial amelioration of inflammation and cell death after brain injury. Nature 223-228.

50. Henderson, M., Rice, B., Sebastian, A., Sullivan, P. G., King, C., Robinson, R. A., and Reed, T. T. (2016). Neuroproteomic study of nitrated proteins in moderate traumatic brain injured rates treated with gamma glutamyl cysteine ethyl ester administration post injury: insight into the role of glutathione elevation in nitrosative stress. Proteomics Clin Appl 10, 1218-1224.

51. Pandya, J. D., Readnower, R. D., Patel, S. P., Yonutas, H. M., Pauly, J. R., Goldstein, G. A., Rabchevsky, A. G., and Sullivan, P. G. (2014). N-acetylcysteine amide confers neuroprotection, improves bioenergetics and behavioral outcome following TBI. Exp Neurol 257, 105-113.

52. Winter, A. N., Ross, E. K., Daliparthi, V., Sumner, W. A., Kirchhof, D. M., Manning, E., Wilkins, H. M., and Linseman, D. A. (2017). A cystine-rich whey supplement (IMMUNOCAL (®)) provides neuroprotection from diverse oxidative stress-inducing agents in vitro by preserving cellular glutathione. Oxid Med Cell Longev 2017, 3103272.

53. Ban V S, Madden C J, Bailes J E, Batjer H H, Lonser R R (2016) The science and questions surrounding chronic traumatic encephalopathy. Neurosurg Focus 40: E15.

54. Baruchel S, Viau G (1996) In vitro selective modulation of cellular glutathione by a humanized native milk protein isolate in normal cells and rat mammary carcinoma model. Anticancer Res 16:1095-1100.

55. Barucehl S, Viau G, Olivier R, Bounous G, Wainberg M A (1998) Nutraceutical modulation of glutathione with a humanized native milk serum protein isolate, IMMUNO-CAL®: application in AIDS and cancer," in Oxidative Stress in Cancer, AIDS, and Neurodegenerative Diseases, L. Montagnier, R. Olivier and C. Pasquier, Eds., vol. 1, Chapter 42, pp. 447-462, Marcel Dekker, Inc., New York, NY, USA.

56. Mao X, Hao S, Zhu Z, Zhang H, Wu W, Xu F, Liu B (2015) Procyanidins protects against oxidative damage and cognitive deficits after traumatic brain injury. Brain Inj 29:86-92.

All references cited herein and elsewhere in the specification are herein incorporated by reference in their entireties.

What is claimed is:

1. A method of ameliorating traumatic brain injury (TBI) symptoms in a subject, said method comprising:
assessing the subject's cognitive function pre-TBI;
administering 20 g of a composition consisting of whey protein isolate and/or whey protein concentrate to the subject pre-injury, wherein the composition is administered orally, twice daily for 5 days per week, over a period of 28 days prior to the TBI; and
assessing the subject's cognitive function 10-16 days post-TBI, wherein the subject's cognitive function 10-16 days post-TBI is equal to the subject's cognitive function pre-TBI.

2. The method according to claim 1, wherein the composition is administered at least 4 weeks prior to injury.

3. The method according to claim 1, wherein the composition is administered to the subject beginning at least about 4 weeks prior to injury or prior to performing an activity for which there is a risk of injury.

4. The method according to claim 1, wherein administration of the composition attenuates a reduction in brain GSH/GSSG ratio following injury as compared to an untreated control.

5. The method according to claim 1, wherein administration of the composition attenuates motor function and/or cognitive function deficit following injury as compared to an untreated control.

6. The method according to claim 1, wherein administration of the composition preserves corpus callosum width and/or axonal myelination following injury as compared to an untreated control.

7. The method according to claim 1, wherein administration of the composition attenuates neuron degeneration following injury as compared to an untreated control.

8. The method according to claim 1, wherein administration of the composition reduces Iba1 microglial marker immunoreactivity in the brain following injury as compared to an untreated control.

9. The method according to claim 1, wherein administration of the composition reduces demyelination of the corpus callosum following injury as compared to an untreated control.

10. The method according to claim 1, wherein administration of the composition reduces number of foci of degenerating neurons following injury as compared to an untreated control.

11. The method according to claim 1, wherein the composition comprises a non-denatured whey protein supplement, wherein the whey protein supplement comprises:
about 3.0 g/L of β-lactoglobulin (MW 18,400),
about 1.2 g/L of α-lactalbumin (MW 14,200),
about 0.3 g/L of BSA (bovine serum albumin; MW 69,000),
about 0.2 g/L of Lactoferrin (MW 77,000),
about 0.2 g/L of IgG (MW 160,000),
about 0.6 g/L of PP-3 (proteose-peptone 3; MW 22,000),
about 0.6 g/L of PP-5 (proteose-peptone 5; MW 14,300),
about 0.6 g/L of PP-8f (proteose-peptone 8f; MW 4,100), and
about 1.6 g/L of NPN (non-protein nitrogen).

12. A method of ameliorating traumatic brain injury (TBI) symptoms in a subject, said method comprising:
identifying the subject as being at risk for receiving a TBI based on one or more risk factors;
assessing the subject's cognitive function pre-TBI;
administering 20 g of a composition consisting of a whey protein isolate and/or whey protein concentrate to the subject identified as being at risk for TBI pre-injury, wherein the composition is administered orally, twice daily for 5 days per week, over a period of 28 days prior to the TBI; and
assessing the subject's cognitive function 10-16 days post-TBI, wherein the subject's cognitive function 10-16 days post-TBI is equal to the subject's cognitive function pre-TBI.

13. The method according to claim 12, wherein the one or more risk factors comprise occupational risk, risk associated with planned activities, or a predisposition or susceptibility of the subject to head injury or brain damage.

14. The method according to claim 12, further comprising a step of:

identifying a known risk date on which the subject has elevated risk for TBI based on the one or more risk factors, and identifying a protective treatment start date which is prior to the known risk date;

wherein administration of the composition to the subject in the step of administering begins on or before the protective treatment start date.

15. The method according to claim 14, wherein the protective treatment start date is at least about 4 weeks prior to the known risk date.

16. The method according to claim 14, wherein the protective treatment start date is at least about 4 weeks prior to the known risk date, and the composition is administered at about 20 grams per day for 5 days per week beginning on or before the protective treatment start date.

* * * * *